(12) United States Patent
Black

(10) Patent No.: US 9,513,197 B2
(45) Date of Patent: Dec. 6, 2016

(54) METHODS, DEVICES, AND SYSTEMS FOR MIXING FLUIDS

(71) Applicant: Theranos, Inc., Palo Alto, CA (US)

(72) Inventor: Matthew Black, Palo Alto, CA (US)

(73) Assignee: Theranos, inc., Palo Alto, CA (US)

( * ) Notice: Subject to any disclaimer, the term of this patent is extended or adjusted under 35 U.S.C. 154(b) by 0 days.

(21) Appl. No.: 15/069,263

(22) Filed: Mar. 14, 2016

(65) Prior Publication Data

US 2016/0195457 A1     Jul. 7, 2016

Related U.S. Application Data

(63) Continuation of application No. PCT/US2015/059421, filed on Nov. 6, 2015.

(60) Provisional application No. 62/077,093, filed on Nov. 7, 2014.

(51) Int. Cl.
  *G01N 1/38* (2006.01)
  *G01N 35/02* (2006.01)
  (Continued)

(52) U.S. Cl.
  CPC ............. *G01N 1/38* (2013.01); *B01F 11/0074* (2013.01); *B01F 15/00876* (2013.01); *B01L 3/508* (2013.01); *G01N 35/10* (2013.01); *B01L 2300/0848* (2013.01); *B01L 2300/12* (2013.01);
  (Continued)

(58) Field of Classification Search
  CPC .................................. G01N 1/38; G01N 35/02
  USPC .............. 73/864.01, 864.11, 864.21; 422/67, 422/501, 510, 512, 514, 519, 521, 522, 547, 422/549, 552, 553, 554, 558, 560–562; 436/43, 49, 165, 180
  See application file for complete search history.

(56) References Cited

U.S. PATENT DOCUMENTS 2,137,773 A  * 11/1938 Jones ...................... A61B 5/20
                                                           33/720
3,190,731 A  *  6/1965 Weiskopf ................ B01L 3/508
                                                           422/557
(Continued)

FOREIGN PATENT DOCUMENTS

JP          H08201388          8/1996
JP          2002228670 A        8/2002

OTHER PUBLICATIONS

International Search Report and Written Opinion dated Feb. 23, 2016 for PCT/US2015/059421.
(Continued)

*Primary Examiner* — Arlen Soderquist

(57) ABSTRACT

Improved methods, devices, and systems for mixing fluids, including small volumes of fluid, are provided. Pressing a pipette tip against an inner surface of a mixing vessel allows pressure to be applied within the tip. Greater pressure may be built-up than would be possible without engaging the tip with the mixing vessel. Disengaging the tip allows fluid flow through the tip, providing improved fluid mixing as compared to methods lacking engagement of a pipette tip with an inner surface of a mixing vessel while applying pressure within the pipette tip.

Mixing vessels having features on an inner surface that are configured to engage a pipette tip, and to occlude an orifice of a pipette tip, are provided. Sample analysis devices and systems including pipette tips and mixing vessels configured to engage each other for pressure application within the tip are provided.

10 Claims, 14 Drawing Sheets

(51) Int. Cl.
*G01N 35/10* (2006.01)
*B01F 11/00* (2006.01)
*B01F 15/00* (2006.01)
*B01L 3/00* (2006.01)

(52) U.S. Cl.
CPC ... *G01N 2001/386* (2013.01); *G01N 2035/106* (2013.01)

(56) References Cited

U.S. PATENT DOCUMENTS

| | | | | |
|---|---|---|---|---|
| 3,356,462 | A * | 12/1967 | Cooke | B01L 3/5085 206/509 |
| 3,521,785 | A * | 7/1970 | Soelter | B01L 3/5082 211/74 |
| 4,007,639 | A * | 2/1977 | Haeckel | A61B 5/1411 422/931 |
| 4,094,641 | A * | 6/1978 | Friswell | B01L 3/508 215/12.1 |
| 4,154,795 | A * | 5/1979 | Thorne | B01L 3/5085 206/460 |
| 4,227,886 | A * | 10/1980 | Bullock | G01N 21/9018 134/113 |
| 4,373,931 | A * | 2/1983 | Takekawa | B01L 3/5021 356/246 |
| 4,466,740 | A * | 8/1984 | Kano | G01N 33/5304 356/246 |
| 4,539,855 | A * | 9/1985 | Jacobs | G01N 35/00029 141/130 |
| 4,586,546 | A * | 5/1986 | Mezei | G01N 35/1011 141/2 |
| 4,639,242 | A * | 1/1987 | Babson | B01L 3/5021 215/40 |
| 4,678,559 | A * | 7/1987 | Szabados | G01N 1/28 209/17 |
| 4,707,337 | A * | 11/1987 | Jeffs | B01L 3/0275 422/525 |
| 4,713,974 | A * | 12/1987 | Stone | G01N 30/24 422/64 |
| 4,758,409 | A * | 7/1988 | Uffenheimer | B01L 3/508 206/438 |
| 4,968,486 | A * | 11/1990 | Zander | B01L 3/5082 206/521 |
| 5,012,845 | A * | 5/1991 | Averette | G01N 35/1079 141/130 |
| 5,102,623 | A * | 4/1992 | Yamamoto | B01L 7/52 141/130 |
| 5,167,926 | A * | 12/1992 | Kimura | G01N 1/28 422/504 |
| 5,382,409 | A * | 1/1995 | Baxter | B01L 3/5082 220/732 |
| 5,452,619 | A * | 9/1995 | Kawanabe | G01N 33/491 73/863 |
| 5,555,767 | A | 9/1996 | Makino et al. | |
| 5,750,075 | A * | 5/1998 | Spike | B01L 3/508 206/446 |
| 5,871,700 | A * | 2/1999 | Konrad | B01L 9/06 206/446 |
| 5,915,583 | A * | 6/1999 | Cloonan | B01L 9/06 220/23.86 |
| 6,006,800 | A * | 12/1999 | Nakano | B65B 43/42 141/130 |
| 6,143,250 | A * | 11/2000 | Tajima | B01L 3/0275 220/23.2 |
| 6,652,809 | B1 * | 11/2003 | Comley | B01L 9/065 422/547 |
| 6,883,958 | B2 * | 4/2005 | Mayer | B01D 61/18 366/197 |
| 8,187,460 | B2 * | 5/2012 | Kreuwel | B01L 3/5085 210/222 |
| 8,216,528 | B2 * | 7/2012 | Shomi | C12M 45/02 422/527 |
| 8,840,848 | B2 * | 9/2014 | Kraihanzel | B01L 3/5085 422/131 |
| 2013/0137110 | A1 * | 5/2013 | Kraihanzel | B01L 3/5085 435/6.12 |
| 2015/0369835 | A1 * | 12/2015 | Knight | B01L 3/50825 436/43 |

OTHER PUBLICATIONS

PCT Application No. US15/59421 filed on Nov. 6, 2015.

* cited by examiner

METHODS, DEVICES, AND SYSTEMS FOR MIXING FLUIDS

CROSS-REFERENCE TO RELATED APPLICATIONS

This application claims priority to, and the benefit of, U.S. Provisional Application Ser. No. 62/077,093, filed Nov. 7, 2014, the entire contents of which is hereby incorporated by reference in its entirety.

BACKGROUND

Fluid mixing has many industrial, chemical, and clinical applications. Mixing small volumes of fluids may present different challenges as compared to mixing large volumes of fluids. For example, large fluid volumes may be mixed in containers of sizes that allow insertion of paddles or stirring bars; however, small fluid volumes, and containers to hold such volumes, may not be readily amenable to the insertion of mechanical mixing implements. Current methods for mixing small fluid volumes present problems not typically encountered with larger volumes of fluid. Accordingly, improved methods and devices for mixing small volumes of fluid, and for mixing small volumes of fluid in small containers are desired.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Applicant provides methods, devices, and systems for mixing fluids; in embodiments, the methods, devices, and systems are suitable for use with small volumes of fluid, and are suitable for mixing small fluid volumes. Prior methods of mixing, including prior methods using automatic sample handling and automatic sample analysis devices and systems, avoided jamming a pipette tip into the wall of a mixing vessel. Applicant surprisingly has discovered that mixing may be improved by pressing a distal portion of a pipette tip against an inner surface of a mixing vessel effective to occlude the orifice of the pipette tip, applying pressure within the mixing vessel, and then retracting the pipette tip effective to remove the occlusion of the orifice of the pipette tip, allowing fluid flow through the orifice. Such fluid flow following retraction of the pipette tip is believed to be of greater force, or volume, or duration, or combinations thereof, than such fluid flow would be in similar circumstances if the pipette tip had not first been pressed against the mixing vessel wall.

Accordingly, Applicant discloses improved methods, devices, and systems for mixing fluids, including mixing small volumes of fluid. In embodiments, the improved methods include methods for mixing small fluid volumes in small containers (such as small volume mixing vessels). A tube, conduit, pipette tip, or other tool or implement suitable for transfer of fluid may be used in conjunction with a mixing vessel to mix fluids; the term "pipette tip" is used herein to indicate any such tool or implement suitable for transfer of fluid, where the fluid transfer tool or implement has a portion with an orifice.

A pipette tip may be pressed against an inner surface of a mixing vessel, engaging the pipette tip with the mixing vessel, effective to occlude the orifice of the pipette tip. Pressure may be applied within the pipette tip while the pipette tip is engaged with the mixing vessel (i.e., while the pipette tip orifice is occluded by being pressed against an inner surface of the mixing vessel). A greater amount of pressure may be built-up within the pipette tip than would be possible were the pipette tip not engaged with the mixing vessel. Disengagement of the pipette tip from the inner surface of the mixing vessel allows fluid flow from the pipette tip (where the pressure within the pipette tip is positive pressure) or allows fluid flow into the pipette tip (where the pressure within the pipette tip is negative pressure), thereby providing mixing of fluid. Application of positive and negative pressure within the pipette tip may be alternated, in order to provide a cycle, or repeated cycles, of alternating positive and negative pressure within a pipette tip, providing a cycle, or repeated cycles, of alternating expulsion of fluid from the pipette tip (with positive pressure) and aspiration of fluid into the pipette tip (with negative pressure). The pipette tip may be pressed against an inner surface of the mixing vessel prior to one, two, or more, applications of pressure during such a cycle or during repeated cycles, of alternating positive and negative pressure. In embodiments, the pipette tip may be pressed against an inner surface of the mixing vessel prior to each application of pressure during such a cycle or during repeated cycles, of alternating positive and negative pressure. The present methods provide improved fluid mixing as compared to methods lacking engagement of a pipette tip with an inner surface of a mixing vessel while applying pressure within the pipette tip.

Thus, in embodiments, a method of mixing fluid comprises engaging a pipette tip with a mixing vessel by pressing a pipette tip against an inner surface of a mixing vessel, effective to occlude the orifice at the end of the pipette tip; applying pressure within the pipette tip; and disengaging the pipette tip from the inner surface of a mixing vessel, effective to remove the occlusion of the orifice at the end of the pipette tip, while maintaining the pressure within the pipette tip, whereby fluid flows through the pipette tip orifice effective to mix fluid. The fluid flow through the pipette tip orifice following disengagement according to the methods disclosed herein is believed to be greater than fluid flow through the pipette tip orifice under the same pressure but in the absence of the present methods (e.g., in the absence of pressure application while the pipette is engaged with an inner surface of the mixing vessel).

In embodiments, a first fluid is present within the pipette tip, and a second fluid is present in the mixing vessel. In embodiments in which a first fluid is present within the pipette tip, and a second fluid is present in the mixing vessel, positive pressure within the pipette tip is effective to expel the first fluid from the pipette tip orifice and to effect mixing of the first fluid and the second fluid within the mixing vessel. In embodiments in which a first fluid is present within the pipette tip, and a second fluid is present in the mixing vessel, negative pressure within the pipette tip is effective to aspirate the second fluid from the mixing vessel into the pipette tip orifice and to effect mixing of the first fluid and the second fluid within the pipette tip.

One or more steps of the methods disclosed herein may be repeated. For example, in embodiments, application of positive pressure may be alternated with application of negative pressure, effective that fluid may be expelled from, and then aspirated into, the pipette tip via the pipette tip orifice. Such alterations may be repeated once, twice, or more times. For a further example, in embodiments, application of negative pressure may be alternated with application of positive pressure, effective that fluid may be aspirated into, and then expelled from, the pipette tip via the pipette tip orifice. Such alterations may be repeated once, twice, or more times. In embodiments, the pipette tip is pressed against an inner surface of the mixing vessel prior to the application of pressure for each alteration of pressure. In embodiments, the pipette tip is pressed against an inner surface of the mixing vessel prior to the application of pressure for one alteration, or for some of the alterations of pressure, but not for all alterations of pressure.

It will be understood that not all of the fluid originally present within a pipette tip need be expelled from the pipette tip during a first expulsion, or during subsequent expulsions, if any, and that not all of the fluid originally present within a mixing vessel need be aspirated into the pipette tip. It will be understood that, following expulsion of a first fluid into a mixing vessel containing a second fluid, fluid aspirated into a pipette tip may be a mixture of first and second fluids. It will be understood that the amount of fluid aspirated into a pipette tip, following a prior expulsion of fluid from a pipette tip, may be a greater amount of fluid than was expelled; may be the same amount of fluid as was expelled; or may be a lesser amount of fluid than was expelled.

In embodiments, a pipette tip may include a fluid, and a mixing vessel may be empty prior to expulsion of fluid from the pipette tip. Aspiration of fluid into a pipette tip may be performed following expulsion of fluid into an empty mixing vessel. In embodiments, a mixing vessel may include a fluid, and a pipette tip may be empty prior to aspiration of fluid from the mixing vessel into the pipette tip. Expulsion of fluid into a mixing vessel may be performed following aspiration of fluid into an empty pipette tip. Such aspiration and expulsion operations may be repeated for further mixing.

Accordingly, Applicant discloses herein that the amount and completeness of mixing is increased, and the mixing of fluid is improved, by first occluding the orifice of a fluid conduit (e.g., a pipette tip) while applying increased (positive) pressure to fluid within the fluid conduit, and then removing the occlusion allowing fluid to flow out of the fluid conduit and into a mixing vessel, as compared to the mixing performed by merely applying pressure to fluid within the fluid conduit to effect flow into a mixing vessel, in the absence of occluding the orifice for a period of time while pressure is applied.

Accordingly, Applicant discloses herein that the amount and completeness of mixing is increased, and the mixing of fluid is improved, by first occluding the orifice of a fluid conduit (e.g., a pipette tip) while applying suction (negative pressure) to fluid within the fluid conduit, and then removing the occlusion allowing fluid to flow out of the mixing vessel and into the fluid conduit, as compared to the mixing performed by merely applying negative pressure to fluid within the fluid conduit to effect flow from a mixing vessel, in the absence of occluding the orifice for a period of time while pressure is applied.

Occlusion of a pipette tip orifice is accomplished, at least in part, by pressing the distal (orifice) end of a pipette tip against an inner surface, or portion thereof, of the mixing vessel. Pressing the pipette tip against an inner surface, or portion thereof, of the mixing vessel is effective to provide a seal between the outer surface of the pipette tip orifice and at least a portion of the inner surface of the mixing vessel, effective to prevent fluid flow through the orifice during application of pressure within the pipette tip. In embodiments, pressing the pipette tip more forcefully against the inner surface of the mixing vessel increases the effectiveness of the seal, i.e., greater force pressing a pipette tip against the inner surface of the mixing vessel provides a better seal than does a lesser force pressing a pipette tip against the inner surface of the mixing vessel. A seal that prevents fluid flow through the orifice during the application of greater pressure within the pipette tip is a better seal than one that only prevents fluid flow through the orifice during the application of lesser, but not greater, pressure within the pipette tip.

In embodiments, the inner surface of a mixing vessel, or a portion of the inner surface of the mixing vessel, may be shaped or sized effective to engage with and occlude the orifice of a pipette tip when the pipette tip is pressed against that surface or portion thereof. In embodiments, the inner surface of a mixing vessel, or a portion of the inner surface of the mixing vessel, may include a feature or element configured to engage with and occlude the orifice of a pipette tip when the pipette tip is pressed against that feature or element. In embodiments, a feature configured to engage with and occlude a pipette tip orifice has a surface complementary to the outer surface of the pipette tip orifice, so that, when the pipette tip is pressed against the feature, the outer surface of the pipette tip orifice makes a seal against the feature, where the seal is effective to prevent fluid flow through the orifice during application of pressure within the pipette tip. As described in the following, features are described with respect to the inner surface of a mixing vessel, or to that portion of the inner surface of the mixing vessel adjacent to the feature. For example, such a feature or element may be a raised surface configured to engage with and occlude a pipette tip orifice (e.g., a bump, a ridge, or a step); may be a slanted surface configured to engage with and occlude a pipette tip orifice (e.g., a ramp, or a slanted wall); may be a depression, or other concave feature, configured to engage with and occlude a pipette tip orifice (e.g., a slot, a pit, or a rounded or conical depression); may be a spike, or cone, or other convex feature configured to engage with and occlude a pipette tip orifice (including, in embodiments, to at least partially protrude into the orifice); and may be any other feature configured to engage with and occlude a pipette tip orifice when the pipette tip is pressed against the feature.

Accordingly, Applicant provides a method of mixing a fluid, comprising: Pressing a pipette tip of against an inner surface of a mixing vessel, wherein i) the pipette tip has an interior passage therethrough, a distal end with a lip defining an orifice, wherein the orifice is continuous with and connected to the interior passage, and a proximal end connected to the interior passage and configured to engage with a nozzle; and ii) the pipette tip is held by a nozzle, the nozzle comprising an operable fluid connection with a source of positive-pressure or suction; and wherein when a pipette tip is held by the nozzle, an operable fluid connection is provided between the nozzle, the orifice, the interior passage, the distal portion and the source of positive-pressure or suction; wherein the pressing pressed the lip against the inner surface of the mixing vessel, effective to occlude the orifice; Applying pressure to fluid within one or more of the nozzle, the distal portion, the interior passage, and the orifice; Removing the pipette tip from contact with the inner surface of a mixing vessel, effective to remove the occlusion of the orifice effective that fluid flows through the orifice; Whereby fluid is mixed within the mixing vessel.

Accordingly, Applicant provides a method of mixing a fluid, the sequence of steps comprising: Pressing a pipette tip of against an inner surface of a mixing vessel, wherein i) the pipette tip has an interior passage therethrough, a distal end with a lip defining an orifice, wherein the orifice is continuous with and connected to the interior passage, and a proximal end connected to the interior passage and configured to engage with a nozzle; and ii) the pipette tip is held by a nozzle, the nozzle comprising an operable fluid connection with a source of positive-pressure or suction; and wherein when a pipette tip is held by the nozzle, an operable fluid connection is provided between the nozzle, the orifice, the interior passage, the distal portion and the source of positive-pressure or suction; wherein the pressing pressed the lip against the inner surface of the mixing vessel, effective to occlude the orifice; then Applying pressure to fluid within one or more of the nozzle, the distal portion, the interior passage, and the orifice; then Removing the pipette tip from contact with the inner surface of a mixing vessel, effective to remove the occlusion of the orifice effective that fluid flows through the orifice; Whereby fluid is mixed within the mixing vessel.

In embodiments, one or more of these steps may be repeated; for example, where positive pressure is applied effective that fluid is expelled through the orifice, subsequent further steps of pressing a pipette tip against an inner surface of a mixing vessel, applying negative pressure, and removing the pipette tip from contact with the inner surface of the mixing vessel, are effective to provide aspiration of fluid into the pipette tip through the orifice. In embodiments, where negative pressure is applied effective that fluid is aspirated through the orifice, subsequent further steps of pressing a pipette tip against an inner surface of a mixing vessel, applying positive pressure, and removing the pipette tip from contact with the inner surface of the mixing vessel, are effective to provide expulsion of fluid from the pipette tip through the orifice.

In embodiments of the methods of mixing fluids disclosed herein, the pressure is positive pressure effective to induce fluid flow out of the orifice and into the mixing vessel. In embodiments, the mixing vessel contains a first fluid, the fluid handling apparatus contains a second fluid, and the mixing comprises mixing the first fluid and the second fluid within the mixing vessel. In embodiments, the pressure is negative pressure effective to induce fluid flow into the orifice and out of the mixing vessel. In embodiments, the mixing vessel contains a first fluid, and the fluid handling apparatus contains a second fluid, and the fluid flow is effective to mix the first fluid and the second fluid. In embodiments, the methods disclosed herein may be repeated, and alternated, so that, e.g., repeated performance of the methods provide expulsion of fluid from a pipette tip orifice (with positive pressure application) followed by aspiration of fluid from a pipette tip orifice (with negative pressure application); or, e.g., repeated performance of the methods provide aspiration of fluid into a pipette tip orifice (with negative pressure application) followed by expulsion of fluid from a pipette tip orifice (with positive pressure application);

In embodiments of the methods of mixing fluids comprising applying negative pressure, the methods further comprise applying positive pressure after applying negative pressure, effective to induce fluid flow out of the orifice and into the mixing vessel, effective to mix the first fluid and the second fluid within the mixing vessel. In embodiments of the methods of mixing fluids comprising applying positive pressure, the methods further comprise applying negative pressure after applying positive pressure, effective to induce fluid flow into the orifice and out of the mixing vessel following expulsion of fluid from the pipette tip. In embodiments of the methods of mixing fluids disclosed herein, applying pressure comprises alternating application of positive pressure and negative pressure, effective to expel fluid from the pipette tip orifice during application of positive pressure, and effective to aspirate fluid into the pipette tip orifice during application of negative pressure, wherein the mixing the first fluid and the second fluid comprises mixing within the mixing vessel. In embodiments, the methods of mixing fluids further comprise applying positive pressure, effective to induce fluid flow out of the orifice and into the mixing vessel, effective to further mix the first fluid and the second fluid within the mixing vessel following aspiration of fluid into the pipette tip. In embodiments of the methods of mixing fluids disclosed herein, applying pressure comprises alternating application of negative pressure and positive pressure, effective to aspirate fluid from the pipette tip orifice during application of negative pressure, and effective to expel fluid into the pipette tip orifice during application of positive pressure, wherein the mixing the first fluid and the second fluid comprises mixing within the mixing vessel.

Applicant further discloses a method of mixing fluids using an automatic sample analysis device, comprising: Providing an automatic sample analysis device comprising a mixing vessel having an interior surface, and a pipette having a tip with an orifice; Pressing the pipette tip into the mixing vessel effective that the pipette tip contacts the interior surface effective to occlude the orifice; Applying pressure to fluid within the pipette tip; Displacing the pipette tip effective to remove the occlusion of the orifice and to allow fluid flow through the orifice, Whereby fluid is mixed within the mixing vessel.

Applicant further discloses a method of mixing fluids using an automatic sample analysis device, the sequence of steps comprising: Providing an automatic sample analysis device comprising a mixing vessel having an interior surface, and a pipette having a tip with an orifice; then Pressing the pipette tip into the mixing vessel effective that the pipette tip contacts the interior surface effective to occlude the orifice; then Applying pressure to fluid within the pipette tip; then Displacing the pipette tip effective to remove the occlusion of the orifice and to allow fluid flow through the orifice, Whereby fluid is mixed within the mixing vessel.

In embodiments, Applicant discloses herein methods of mixing fluids by an automatic sample analysis device, the methods comprising: Pressing a tip of a pipette against an interior surface of a mixing vessel, said pipette having a tip, an interior containing a fluid, and an orifice in said tip providing access to said pipette interior, said mixing vessel having an interior with an interior surface, effective that said pipette tip contacts said interior surface effective to occlude said orifice, wherein said pipette is operably connected to an automated pipette mechanism, said automated pipette mechanism comprising part of an automatic sample analysis device; then Applying pressure to the fluid within said pipette tip; then Displacing said pipette tip effective to remove said occlusion of said orifice and to allow fluid flow through said orifice, Whereby fluid is mixed within said mixing vessel. In embodiments, Applicant discloses methods of mixing fluids by an automatic sample analysis device, wherein said pressure comprises positive pressure effective to expel fluid from said pipette tip through said orifice and into said mixing vessel. In embodiments, Applicant discloses methods of mixing fluids by an automatic sample analysis device, wherein said pressure comprises negative pressure effective to draw fluid from said mixing vessel and into said pipette tip through said orifice. In embodiments, Applicant discloses methods of mixing fluids by an automatic sample analysis device, the methods further comprising alternating application of positive pressure and of negative pressure, wherein said alternating comprises a) applying positive pressure following application of negative pressure, wherein applying positive pressure is effective to expel fluid from said pipette tip through said orifice and into said mixing vessel, or b) applying negative pressure following said application of positive pressure, wherein applying negative pressure is effective to aspirate fluid from said mixing vessel and into said pipette tip through said orifice. In embodiments, Applicant discloses methods of mixing fluids by an automatic sample analysis device, wherein the interior surface of the mixing vessel has a protrusion which extends into the interior of the mixing vessel, wherein said protrusion is configured to engage and occlude an orifice of a pipette tip when a pipette tip is placed onto or over the protrusion. In embodiments, Applicant discloses methods of mixing fluids by an automatic sample analysis device, wherein the interior surface of the mixing vessel has a depression which extends away from the rest of the interior of the mixing vessel, wherein said depression is configured to engage and occlude an orifice of a pipette tip when a pipette tip is placed onto or into the depression. In embodiments, Applicant discloses methods of mixing fluids by an automatic sample analysis device, wherein a pipette tip is engaged with a protrusion on an interior surface of a mixing vessel, and wherein said pressure comprises positive pressure effective to expel fluid from said pipette tip through said orifice and into said mixing vessel. In embodiments, Applicant discloses methods of mixing fluids by an automatic sample analysis device, wherein a pipette tip is engaged with a protrusion on an interior surface of a mixing vessel, and wherein said pressure comprises negative pressure effective to draw fluid from said mixing vessel and into said pipette tip through said orifice. In embodiments, Applicant discloses methods of mixing fluids by an automatic sample analysis device, wherein a pipette tip is engaged with a depression on an interior surface of a mixing vessel, and wherein said pressure comprises positive pressure effective to expel fluid from said pipette tip through said orifice and into said mixing vessel. In embodiments, Applicant discloses methods of mixing fluids by an automatic sample analysis device, wherein a pipette tip is engaged with a depression on an interior surface of a mixing vessel, and wherein said pressure comprises negative pressure effective to draw fluid from said mixing vessel and into said pipette tip through said orifice.

In embodiments of methods of mixing fluids using an automatic sample analysis device, the pressure comprises positive pressure effective to expel fluid from the pipette tip through the orifice and into the mixing vessel. In embodiments of methods of mixing fluids using an automatic sample analysis device where the pressure comprises positive pressure, the methods further comprise applying negative pressure following the applying of positive pressure, wherein applying negative pressure is effective to aspirate fluid from the mixing vessel through the orifice and into the pipette tip. In embodiments, the pressure comprises negative pressure effective to draw fluid from the mixing vessel and into the pipette tip through the orifice. In embodiments of methods of mixing fluids using an automatic sample analysis device where the pressure comprises negative pressure, the methods further comprise applying positive pressure following the applying of negative pressure, wherein applying positive pressure is effective to expel fluid from the pipette tip through the orifice and into the mixing vessel. In embodiments of methods of mixing fluids using an automatic sample analysis device, the methods comprise alternating application of positive pressure and of negative pressure, wherein said alternating comprises a) applying positive pressure following application of negative pressure, wherein applying positive pressure is effective to expel fluid from said pipette tip through said orifice and into said mixing vessel, or b) applying negative pressure following said application of positive pressure, wherein applying negative pressure is effective to aspirate fluid from said mixing vessel and into said pipette tip through said orifice.

Applicant further discloses an automatic sample analysis device comprising a mixing vessel having an interior cavity having an interior surface, and a pipette tip having a lip defining an orifice, wherein the automatic sample analysis device is configured to mix fluids within a mixing vessel following occlusion of the orifice. In embodiments of the automatic sample analysis devices disclosed herein, the mixing vessel comprises a feature configured to engage the pipette tip, effective that when the lip of the pipette tip is pressed against the interior surface, the orifice is occluded effective to prevent fluid flow through the orifice. In embodiments of the automatic sample analysis devices disclosed herein, the feature configured to engage the lip of the pipette tip of the fluid handling apparatus comprises a tapered indentation in the interior surface of the vessel. In embodiments of the automatic sample analysis devices disclosed herein, the feature configured to engage the lip of the pipette tip comprises a convex feature extending into the interior cavity of the mixing vessel and configured to extend at least partially into the orifice effective to occlude the orifice when the pipette tip is pressed against the interior surface, the orifice is occluded effective to prevent fluid flow through the orifice. In embodiments of the automatic sample analysis devices disclosed herein, the feature configured to engage the tip of the fluid handling apparatus comprises a conical or tapered feature extending from into the interior of the mixing vessel. In embodiments of the automatic sample analysis devices disclosed herein, the tapered indentation in the interior surface of the vessel further comprises a convex feature extending towards the interior cavity of the mixing vessel, wherein the convex feature is configured to extend at least partially into the orifice effective to occlude the orifice.

Applicant further discloses a mixing vessel comprising an interior cavity having an interior surface, wherein the interior surface comprises a feature configured to engage a pipette tip having a lip defining an orifice, effective that when the lip of the pipette tip is pressed against the interior surface, the orifice is occluded effective to prevent fluid flow through the orifice. In embodiments of the mixing vessels disclosed herein, the feature configured to engage the lip of the pipette tip of the fluid handling apparatus comprises a tapered indentation in the interior surface of the mixing vessel. In embodiments of the mixing vessels disclosed herein, the feature configured to engage the lip of the pipette tip comprises a convex feature extending into the interior cavity of the mixing vessel and configured to extend at least partially into the orifice effective to occlude the orifice when the pipette tip is pressed against the interior surface, the orifice is occluded effective to prevent fluid flow through the orifice. In embodiments of the mixing vessels disclosed herein, the feature configured to engage the tip of the fluid handling apparatus comprises a conical or tapered feature extending from the interior surface into the interior of the mixing vessel. In embodiments of the mixing vessels disclosed herein, the tapered indentation in the interior surface of the vessel further comprises a convex feature extending towards the interior cavity of the mixing vessel, wherein the convex feature is configured to extend at least partially into the orifice effective to occlude the orifice.

Applicant further discloses a system for mixing small volumes of fluid, the system comprising: i) a fluid handling apparatus comprising a base; at least one head operably connected with the base; at least one nozzle operably connected with the at least one head and having a pathway for fluid flow between the nozzle and the head; wherein the at least one head comprises mechanical and structural components operable with each nozzle, and wherein the at least one nozzle is configured to engage a pipette tip, effective that a pipette tip may be held by a nozzle; a pipette tip having an interior passage therethrough and comprising a proximal end configured to engage with a nozzle effective that the pipette tip may be held by the nozzle, and a distal end having a lip defining an orifice, wherein the orifice is continuous with and connected to the interior passage, wherein when a pipette tip is held by a nozzle, i) a continuous pathway for fluid flow is provided between the orifice of the pipette tip, the pipette tip interior passage, the nozzle holding the pipette tip, and the head associated with the nozzle; and ii) the pipette tip may be sealed to the nozzle effective that positive-pressure or suction within the pipette tip is effective to cause fluid flow into or out of the orifice of the pipette tip without dislodging the pipette tip from the nozzle; and a source of positive-pressure or suction in fluid contact with one or more of the pipette tip, the nozzle, the head, and the base, effective that the source may apply positive-pressure or suction within the pipette tip effective to cause fluid flow into or out of the orifice of the pipette tip, and ii) a mixing vessel comprising an interior portion defined by an interior surface having an interior wall and a bottom, the interior portion having an engagement region, wherein the engagement region comprises a concave or convex feature configured to engage the lip of the pipette tip, effective that when the lip of the pipette tip is pressed against the concave or convex feature, the orifice is occluded effective to prevent fluid flow through the orifice. In embodiments of the systems for mixing small volumes of fluid disclosed herein, the pipette tip may be releasably engaged with the at least one nozzle, effective that the pipette tip may be engaged with a nozzle, and may be disengaged from a nozzle. In embodiments of the systems for mixing small volumes of fluid disclosed herein, application of positive-pressure or suction within the interior passage of the pipette tip does not cause disengagement of the pipette tip. In embodiments of the systems for mixing small volumes of fluid disclosed herein, the at least one nozzle is movable with respect to the head to which it is operably connected, is movable with respect to the base to which it is operably connected, or both. In embodiments of the systems for mixing small volumes of fluid disclosed herein, the at least one head is movable with respect to the base to which it is operably connected. In embodiments of the systems for mixing small volumes of fluid disclosed herein, the fluid handling apparatus comprises a component of an automatic sample analysis device, wherein the base is movable with respect to other components of the automatic sample analysis device. In embodiments of the systems for mixing small volumes of fluid disclosed herein, the base is movable within the automatic sample analysis device. In embodiments of the systems for mixing small volumes of fluid disclosed herein, the engagement region of the interior surface of the mixing vessel comprises a concave feature. In embodiments of the systems for mixing small volumes of fluid disclosed herein, the engagement region of the interior surface of the mixing vessel comprises a convex feature. In embodiments of the systems for mixing small volumes of fluid disclosed herein, the concave feature comprises a tapered indentation in a wall or in the bottom of the vessel. In embodiments of the systems for mixing small volumes of fluid disclosed herein, the convex feature comprises a feature extending from a wall or from the bottom of the mixing vessel into the interior of the vessel. In embodiments of the systems for mixing small volumes of fluid disclosed herein, the feature extending from a wall or from the bottom of the mixing vessel into the interior of the vessel comprises a flat portion. In embodiments of the systems for mixing small volumes of fluid disclosed herein, at least a portion of the feature extending from a wall or from the bottom of the mixing vessel into the interior of the vessel is configured to extend within the orifice when the pipette tip is pressed onto the wall or bottom of the mixing vessel. In embodiments of the systems for mixing small volumes of fluid disclosed herein, the tapered indentation comprises a flat bottom configured to engage the tip and occlude the orifice.

The methods, devices, and systems disclosed herein provide advantages of improved mixing, including providing more complete mixing, providing faster mixing, and providing other advantages in the mixing of fluids. For example, the methods, devices, and systems disclosed herein may be applied to small fluid volumes, and provide more complete and more rapid mixing of small volumes of fluids. These methods are believed to provide further advantages in reducing the amount of fluid needed, so that, where prior methods required large volumes in order to obtain an effective amount of mixing of two or more fluid volumes, by providing better mixing, the present methods provide mixed fluids while requiring smaller volumes than other methods.

The methods, devices, and systems disclosed herein are useful for mixing fluids, including small volumes of fluids. The methods, devices, and systems disclosed herein are believed to provide improved methods for mixing fluids. For example the methods, devices, and systems disclosed herein are believed to provide improved methods for mixing small volumes of fluids, and are suitable for use with small mixing vessels (i.e., mixing vessels whose fluid-holding capacity is small) are suitable for use with small volumes of fluid reagents, are suitable for use with small volumes of fluid diluents, and are suitable for use with small fluid samples (i.e., small volumes of fluid sample). The methods, devices, and systems for mixing fluids may be used with automatic sample handling devices and systems, and with automatic sample analysis devices and systems.

This Summary is introduces a selection of concepts in a simplified form that are further described below in the Detailed Description. This Summary is not intended to identify key features or essential features of the claimed subject matter, nor is it intended to be used to limit the scope of the claimed subject matter. It should be understood that embodiments described above, other embodiments disclosed herein, and variants thereof, comprise non-limiting examples, and may be adapted to have one or more of the features as described herein, and combinations thereof.

DETAILED DESCRIPTION

Figure 1:
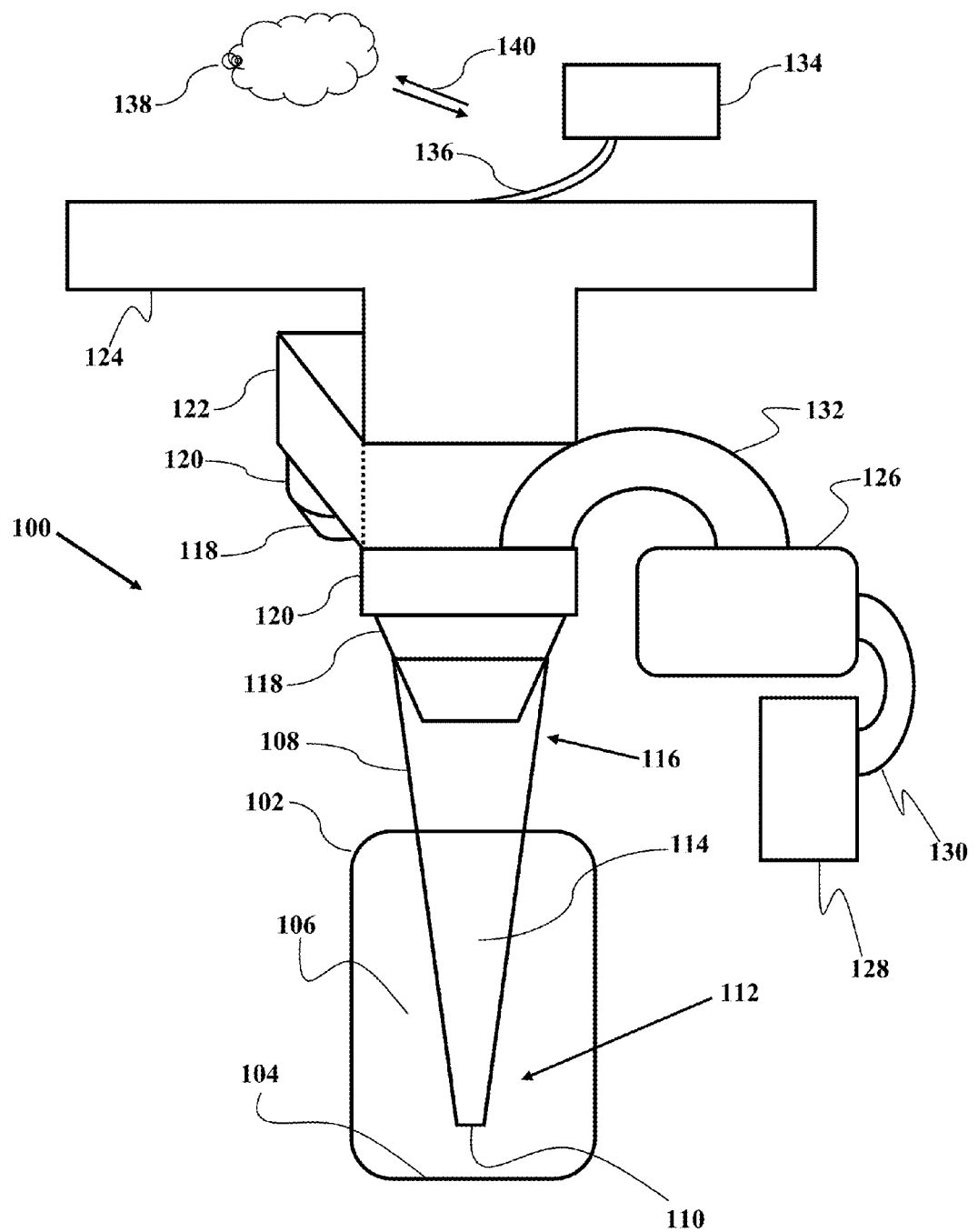
FIG. 1 shows a system having features as disclosed herein, including a mixing vessel with an interior cavity; pipette tip having an orifice and configured to deliver fluid to a mixing vessel; a fluid reservoir operably connected to a pipette tip; a pressure source, where the pressure may be positive pressure or negative pressure (e.g., a pump, a tank containing pressurized gas or fluid under pressure, a tank containing vacuum or other low pressure fluid, or other source of pressure or suction) operably connected to the reservoir and to the pipette or tube, effective to provide pressure or suction; and a conduit connecting the pressure source with the pipette or tube configured to deliver fluid to a mixing vessel. A system as shown in FIG. 1 may include a fluid handling apparatus having one or more bases; a base may include one, two, or more heads, where a head includes mechanical and structural components associated with a nozzle. A head has at least one nozzle, where each nozzle is configured to engage a pipette tip; a pipette tip fits onto, and may be held by, a nozzle. A pipette tip has a proximal end configured to engage with a nozzle, and to provide a fluid pathway, via the nozzle, between the head and the pipette tip. A pipette tip has a distal end with an orifice from which fluid may exit or enter. When held by a nozzle, a pipette tip may be sealed to a nozzle effective that pressure or suction within the tip is effective to cause fluid flow into or out of the orifice of the pipette tip, without dislodging the pipette tip from the nozzle. A base may be movable with respect to (e.g., within) an automatic sample analysis device or system. A head may be movable with respect to a base to which it is operably connected. A nozzle may be movable with respect to a base, or to a head, or both, to which it is operably connected. Movement of a base, a head, a nozzle, or combinations of these, may be used to position a pipette tip to any desired location within an automatic sample analysis device or system.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a method includes a step that may optionally be repeated, the method may be performed with only a single instance of that step, or with two instances of that step, or with three or more instances of that step.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, an "operable connection" refers to a connection between two or more objects (e.g., devices, or components of devices) which allows one object to act on (e.g., effect the position, state, operation, or output of) another object. An operable connection allows two objects to operate together, allowing at least one of the object to act on, or to affect, the other object. For example, an operable connection between an input and an output allows communication (e.g., the transfer of information, data, commands, or other communications) between those two objects. An operable connection may be physical (e.g., mechanical, or fluidic, or structural), electrical, optical, acoustic, or other operable connection, by any means or any modality. An operable connection may be one-way, or may be reciprocal; where reciprocal, the strength or amount of the effect of one object on the other may equal, or may be unequal.

As used herein, the term "pipette tip" will be used to refer generally to any tool or implement for moving fluid, and include without limitation a conduit, pipe, tube, hose, nipple, pipette tip, or other tool or implement for moving fluid, or for directing fluid flow; it will be understood that the term "pipette tip" is meant to be representative of any conduit having an orifice through which fluid may flow. A pipette tip includes an interior region which can hold, and through which can pass, a fluid (e.g., a fluid which may pass through an orifice at a distal portion of the pipette tip). The interior region is configured to hold at least a small volume of fluid.

As used herein, a small volume is a volume of less than about 1 mL, or less than about 750 microliters (µL), or less than about 500 µL, or less than about 400 µL, or less than about 300 µL, or less than about 250 µL, or less than about 150 µL, or less than about 100 µL, or less than about 75 µL, or less than about 50 µL, or less than about 25 µL, or less than about 20 µL, or less than about 15 µL, or less than about 10 µL, or less than about 5 µL, or less than about 4 µL, or less than about 3 µL, or less than about 2 µL, or less than about 1 µL, or less.

A pipette tip may be made from any suitable material, or combination of materials. Suitable materials include, e.g., polypropylene, polycarbonate, polystyrene, polyurethane, polyethylene, polyacrylamide, polyacrylate, polymethacrylate, polymethylmethacrylate (PMMA), poly(4-methylbutene), other acrylic, polydimethysiloxanes (PDMS), polyvinylchloride (PVC), poly(vinyl butyrate) polysulfone, acrylonitrile-butadiene-styrene (ABS), poly(ethylene terephthalate), a fluorocarbon polymer (such as, e.g., polytetrafluoroethylene (PTFE or Teflon®)), nylon, and co-polymers.

As used herein, the term "mixing vessel" will be used to refer generally to any container, or object having a depression, cavity, or reservoir which can hold fluid, and in which a fluid or a plurality of fluids, may be mixed. A mixing vessel has an inner surface which contacts, and holds, fluid container within the vessel. In embodiments, a mixing vessel may have an open side (e.g., an open top) through which fluid may enter or exit the mixing vessel. In embodiments, such an open side (e.g., an open top) may permit introduction of a pipette tip, or portion thereof; for example, introduction of a distal portion of a pipette tip into an interior portion of a mixing vessel allows fluid to flow into or out of the mixing vessel via an orifice in the distal portion of the pipette tip. As disclosed herein, such fluid flow may be used to mix fluid in the mixing vessel.

Mixing vessels disclosed herein may be made from any suitable material; for example, mixing vessels suitable for use in the methods disclosed herein may be made from a material, or a combination of materials, selected from, e.g., polypropylene, polycarbonate, polystyrene, polyurethane, polyethylene, polyacrylamide, polyacrylate, polymethacrylate, polymethylmethacrylate (PMMA), poly(4-methylbutene), other acrylic, polydimethysiloxanes (PDMS), polyvinylchloride (PVC), poly(vinyl butyrate) polysulfone, acrylonitrile-butadiene-styrene (ABS), poly(ethylene terephthalate), a fluorocarbon polymer (such as, e.g., polytetrafluoroethylene (PTFE or Teflon®)), nylon, and a co-polymer.

As used herein, a small volume mixing vessel may be capable of containing a volume of fluid that is less than about 1 mL, or less than about 750 microliters (µL), or less than about 500 µL, or less than about 400 µL, or less than about 300 µL, or less than about 250 µL, or less than about 150 µL, or less than about 100 µL, or less than about 75 µL, or less than about 50 µL, or less than about 25 µL, or less than about 20 µL, or less than about 15 µL, or less than about 10 µL, or less than about 5 µL, or less than about 4 µL, or less than about 3 µL, or less than about 2 µL, or less than about 1 µL, or less.

As used herein, the term "sample" refers to a fluid, tissue, secretion, excretion, or other material collected from a subject. Examples of biological samples include but are not limited to, blood, serum, plasma, bone marrow, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk and/or other secretions or excretions. Biological samples may include nasopharyngeal wash, or other fluid obtained by washing a body cavity or surface of a subject, or by washing a swab following application of the swab to a body cavity or surface of a subject.

As used herein, a "sample" may be, but is not limited to, a fluid sample such as a blood sample, or a portion of a blood sample, and may be of any suitable size or volume, and is preferably of small size or volume. In some embodiments of the methods, devices, and systems disclosed herein, a fluid may be a small volume fluid sample, or no more than a small volume portion of a fluid sample, such as, e.g., a small volume blood sample, or no more than a small volume portion of a blood sample.

As used herein, a small volume fluid sample comprises less than about 1 mL, or less than about 750 µL; or less than about 500 µL; or less than about 400 µL; or less than about 300 µL; or less than about 250 µL; or less than about 150 µL; or less than about 100 µL; or less than about 75 µL; or less than about 50 µL; or less than about 35 µL; or less than about 25 µL; or less than about 20 µL; or less than about 15 µL; or less than about 10 µL; or less than about 8 µL; or less than about 6 µL; or less than about 5 µL; or less than about 4 µL; or less than about 3 µL; or less than about 2 µL; or less than about 1 µL; or less than about 0.8 µL; or less than about 0.5 µL; or comprises a volume of about 0.4 µL or less.

As used herein, a "finger-stick" refers to: i) the act of making a small puncture in the skin of a subject, allowing a small amount (e.g., a droplet, or one, two, or a few drops) of blood to flow and become available for collection; ii) the puncture itself; and iii) the blood collected thereby. A small amount is a small volume, e.g., of blood or other fluid. Blood may be liberated in a finger-stick, for example, by use of a lancet or other sharp implement effective to pierce the skin of a subject. Blood from a finger-stick may be collected, e.g., by needle, syringe, capillary tube, or other method. Blood from a finger-stick may be collected for transport to another location; for storage prior to use or analysis; for immediate use; or for a combination of the same.

When referring to a volume, e.g., a "finger-stick volume" or "the volume of a finger-stick", the term "finger-stick" refers to the volume of a few droplets of blood typically obtained from a finger-stick. A single droplet of blood may have a volume of about 20-50 µL, e.g., about 40 µL. Thus, a few droplets of blood obtained from a finger-stick provide a volume of about 75 µL to about 150 µL, or, in some instances, between about 100-150 µL. Advantages of obtaining blood from a finger-stick include minimal discomfort to the subject and ease of access, as compared to obtaining blood from a vein or artery. Typically, only a small amount of blood is collected in this way (e.g., the amount of blood collected from a finger-stick may be about 250 µL or less, or about 200 µL or less, or about 150 µL or less, or about 100 µL or less, or about 50 µL or less, or about 25 µL or less, or about 15 µL or less, or about 10 µL or less, or about 5 µL or less, or about 3 µL or less, or about 2 µL or less, or about 1 µL or less).

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

In embodiments, clinical samples may be obtained at a point-of-service (POS) location. A POS location may be, for example, a retail pharmacy, a supermarket, a hospital, a clinic, a physician's office, or other location. Clinical samples may be tested at the POS location for multiple markers indicative of agents which may cause one or more of a plurality of diseases (e.g., at least 8, or at least 10, or at least 12, or at least 20, or at least 30, or at least 40, or at least 50, or at least 60, or more markers, indicative of the same or similar numbers of different diseases). The testing may be completed in a short period of time. In embodiments, the short period of time may be measured from the time the sample is inserted into a device or system for performing an analysis. In embodiments, the short period of time may be measured from the time the sample is obtained from the subject.

In embodiments, clinical samples may be analyzed at a POS location. In embodiments, clinical samples obtained at a POS location may be analyzed at the same POS location. In embodiments, clinical samples may be obtained at a point-of-service (POS) location and may be analyzed at a different location. In embodiments, clinical samples may be analyzed in a short period of time, e.g., in a period of time that is less than about 5 hours, or less than about 4 hours, or less than about 3 hours, or less than about 2 hours, or less than about 1 hour, or less than about half an hour.

Description of Embodiments

A pipette tip, a tube, or other fluid handling apparatus having a tip may be pressed against an interior surface of a mixing vessel, effective to occlude the tip and prevent fluid flow out of the fluid handling apparatus. Such a pipette tip, a tube, or other fluid handling apparatus having a tip has an interior space configured to hold fluid. Providing positive pressure or negative pressure (suction) to fluid within a pipette tip does not cause fluid flow through the orifice of the pipette tip while the pipette tip is occluded. An orifice may be occluded by pressing the tip against a surface, such as an interior surface of a mixing vessel. Such occlusion may occur when a tip is pressed against a flat surface; against a curved surface; against a protrusion extending from a surface; against (e.g., into) a depression in a surface; adjacent a protrusion, including adjacent (e.g., between) one or more protrusions, or adjacent a protrusion that partially or completely encloses a distal part of the pipette tip; or against a surface having other configurations. Positive or negative pressure may be provided to fluid within a pipette tip by pump, by piston, by peristaltic action (including by compression of a flexible wall or flexible container, or portion thereof), by providing fluid continuity with a reservoir containing high or low pressure gas or liquid, by providing fluid continuity with a reservoir placed at a higher level or at a lower level than the pipette tip, by osmotic action, or in other ways.

Such altered pressure may comprise increased pressure. Such altered pressure may comprise a vacuum, or partial vacuum. For example, where the altered pressure comprises increased pressure, fluid within the pipette tip becomes pressurized to a greater extent that would be possible with the same gas pressure, or pressurized reservoir, or pump action, were the tip not occluded. Releasing the occlusion by retraction of the pipette tip (or tube) from contact with the vessel interior wall allows fluid to flow out of the tip into the mixing vessel, providing mixing. The amount and speed of fluid flow immediately following release of the occlusion is greater than the amount and speed of flow from such a tip, or tube, in the absence of the occlusion. Thus, occlusion by pressing a tip or tube against an interior wall of a mixing vessel while applying pressure or force to fluid within the pipette tip (or tube) increases mixing. Similarly, where the altered pressure comprises reduced pressure (e.g., suction, such as from at least a partial vacuum), greater suction is built up within the fluid handling apparatus (e.g., pipette tip or tube) than would otherwise be present in the absence of the occlusion, and a greater amount and speed of flow of fluid from within the mixing vessel into the pipette tip or tube occurs than would occur in the absence of such occlusion.

Thus, according to the methods disclosed herein, a small volume of fluid may be mixed within a mixing vessel. In embodiments, the mixing vessel has a small interior volume, sufficient to hold a small volume of fluid. In embodiments, the interior of the mixing vessel may be configured to engage with the tip of a conduit placed within the mixing vessel; for example, an interior surface of a mixing vessel may be configured to engage with a distal portion of a pipette tip effective to occlude the orifice of the pipette tip. In embodiments, a distal portion of a pipette tip may be configured to engage with the interior of the mixing vessel; for example, a pipette tip may be configured to engage with the interior surface of a mixing vessel. A pipette tip, or an interior surface of a mixing vessel, or both, may have a feature, or may have a surface, configured to make an effective seal between the conduit tip and the interior surface of a mixing vessel.

In embodiments, fluid may be introduced by a pipette tip into a mixing vessel under pressure, where the pressure is built up within the pipette tip by pressing a tip of the pipette tip against an inner surface of the mixing vessel. In embodiments, the fluid is aspirated into and from within the mixing vessel, effective to mix the fluid. In embodiments, fluid is introduced into a mixing vessel under pressure, and then aspirated from and into the mixing vessel, effective to mix the fluid within the mixing vessel. In embodiments, a small volume of fluid is introduced in this way into a mixing vessel.

In embodiments, a small volume of fluid initially present within a mixing vessel is aspirated into and from within the mixing vessel, effective to mix the fluid within the mixing vessel. In embodiments, a small volume of fluid is introduced into a mixing vessel, and then aspirated from and into the mixing vessel, effective to mix the fluid within the mixing vessel. In embodiments, a small volume of a first fluid initially present within a mixing vessel is mixed with an additional small volume of a second fluid, and the mixture of the first and second fluid is aspirated into and from within the mixing vessel, effective to mix the fluid within the mixing vessel. In embodiments, a small volume of a first fluid is introduced into a mixing vessel already containing a small volume of a second fluid, and the mixture of the first and second fluid is then aspirated from and into the mixing vessel, effective to mix the fluid within the mixing vessel. In each or any of these embodiments, the fluid (e.g., the small volume of fluid, or the mixture of a small volume of a first fluid with a small volume of a second fluid) may be aspirated into a fluid handling apparatus and out of a fluid handling apparatus two, or three, or four, or five, or more times effective to mix the fluid, and to mix the mixture of a small volume of a first fluid with a small volume of a second fluid.

In embodiments, fluid may be introduced into a mixing vessel, fluid may be removed from a mixing vessel, and fluid may be mixed within a mixing vessel, using a fluid handling apparatus. In embodiments, a fluid handling apparatus may be, or include, without limitation, a pipette tip; a tube; a nozzle; a baffle; and other implements or elements configured to transport fluids, to direct fluid flow, to divert fluid flow from an initial flow path to another flow path, or otherwise to transport, direct, or divert fluid flow. For example, a pipette tip may provide a discontinuous flow pathway for a fluid, e.g., from a reservoir to a mixing vessel. For example, a tube may provide a continuous flow pathway for a fluid, e.g., from a reservoir to a mixing vessel by filling the tube with fluid from the reservoir and flowing that fluid into the mixing vessel, so that, for at least a period of time there is fluid continuity between the fluid within the mixing vessel, the fluid within the tube, and fluid within the reservoir.

In embodiments, a pipette tip may provide a discontinuous flow path by extracting fluid from a reservoir; removing the fluid from contact with the reservoir by removal of the pipette tip from contact with fluid that remains in the reservoir after such extraction; carrying that fluid within the pipette tip from the vicinity of the reservoir to the vicinity of a mixing vessel; and delivering the fluid to the mixing vessel (e.g., by placing the pipette tip near to an opening leading to the interior of the mixing vessel, or inserting the pipette tip at least partially into the interior of the mixing vessel, and ejecting the fluid into the interior of the mixing vessel.

Fluid may be mixed within a mixing vessel using a fluid handling apparatus, such as a fluid handling apparatus having a pipette tip. Flow of fluid from a pipette tip into a mixing vessel may be termed "expulsion." Flow of fluid out of a mixing vessel and into a pipette tip, or tube, or other fluid handling apparatus is termed herein "aspiration", e.g., aspiration of fluid from within a mixing vessel. Flow of fluid within a pipette tip, whether out of the pipette tip into the mixing vessel, into the pipette tip from the mixing vessel, or both, may produce mixing of the fluid by, for example, inducing turbulent flow as the fluid passes through the orifice of the pipette tip (e.g., and into the mixing vessel upon "expulsion", and into the pipette tip upon "aspiration"). Such turbulent flow may provide mixing within the pipette tip, within the mixing vessel, and both within the pipette tip and within the mixing vessel.

Introduction of fluid, or removal of fluid, from a vessel interior by a pipette tip may produce mixing of the fluid. For example, introduction of fluid into a mixing vessel causes that fluid, and any fluid already within the vessel, to flow inside the vessel effective to provide some mixing. Similarly, removal of fluid from a vessel along such a path may produce mixing in the remaining fluid. The interior of a mixing vessel may have an axis of symmetry; for example, a cylindrical cavity, having a circular base, has an axis of symmetry along a vertical line from the center of, and that is perpendicular to, the circular base. Similarly, a conical, or parabolic, or other shaped bottom to an otherwise cylindrical vessel interior has an axis of symmetry which passes from the point of the cone, or peak of the parabola, and through the axis of symmetry of the cylindrical portion. Introduction of fluid at an angle to an axis of symmetry allows the introduced fluid to swirl within the interior cavity, and produces mixing. Similarly, removal of fluid from a vessel along such a path may produce mixing in the remaining fluid.

In embodiments, the containers comprise open containers (e.g., mixing vessels with an opening at one end configured to allow introduction of fluid, or insertion of an implement, or both). In embodiments, the containers comprise closed containers (e.g., containers in which all entry ports are capped, covered, or otherwise enclosed). Mixing fluid within a closed container (e.g., a closed mixing vessel) may be effective to prevent loss of fluid from the container during or resulting from mixing. In embodiments, a closed container may comprise an opening (e.g., an entry port) which is covered by a cap, lid, sheath, or other covering element. In embodiments, a closed container may be able to be opened, e.g., by moving or removing a cap, lid, sheath, or other element from the opening. In embodiments, a closed container may comprise an entry port, or other opening, which may be occluded (i.e., closed) by an implement, such as, e.g., a pipette tip for introduction of fluid, for mixing, or both. Such occlusion may be effected by inserting a conical or otherwise tapered implement into an opening of a mixing vessel, so that the implement has access to the interior of the mixing vessel, but fits snugly against the walls of the opening effective to prevent fluid to flow or splash out of the opening.

Mixing fluids is often performed during analysis of samples, and accurate and reproducible mixing is important in the analysis of samples, such as biological samples. For example, analysis of fluid samples, such as blood or urine samples, or other biological samples, typically entails diluting at least a portion of a fluid sample, or mixing a fluid reagent with at least a portion of a fluid sample, or mixing two or more diluents or reagents for use in analyzing a biological sample. Mixing small samples, and small volumes of reagents, is typically more prone to error or loss (at least on a percentage basis) than is mixing of large volumes of samples and reagents. Automatic sample analysis devices and systems typically provide more accurate and more reproducible mixing than manual methods of mixing.

The methods, devices, and systems disclosed herein may be performed by, and may be used by, automatic sample analysis devices and automatic sample analysis systems.

Automatic Sample Analysis Devices and Systems

The assays and methods disclosed herein may be performed on a device, or on a system, for processing a sample. Mixing vessels, pipette tips, and other tools and implements for mixing fluids disclosed herein may be used by automatic sample analysis devices and systems in the performance of the methods disclosed herein. The assays and methods disclosed herein can be readily incorporated into and used in device for processing a sample, or a system for processing a sample, which may be an automatic sample analysis device, or may be an automatic sample analysis system.

Accordingly, an automatic sample analysis device, an automatic sample analysis system, an automatic sample analysis device, or an automatic sample analysis system may be useful for the practice of the methods disclosed herein. For example, a device may be useful for receiving a sample. A device may be useful for preparing, or for processing a sample. A device may be useful for performing an assay on a sample. A device may be useful for obtaining data from a sample. A device may be useful for transmitting data obtained from a sample. A device may be useful for disposing of a sample following processing or assaying of a sample.

A device may be part of a system, a component of which may be an automatic sample analysis device. A device may be an automatic sample analysis device. An automatic sample analysis device may be configured to facilitate collection of a sample, prepare a sample for a clinical test, or effect a chemical reaction with one or more reagents or other chemical or physical processing, as disclosed herein. An automatic sample analysis device may be configured to obtain data from a sample. An automatic sample analysis device may be configured to transmit data obtained from a sample. An automatic sample analysis device may be configured to analyze data from a sample. An automatic sample analysis device may be configured to communicate with another device, or a laboratory, or an individual affiliated with a laboratory, to analyze data obtained from a sample.

An automatic sample analysis device may be configured to be placed in or on a subject. An automatic sample analysis device may be configured to accept a sample from a subject, either directly or indirectly. A sample may be, for example, a blood sample (e.g., a sample obtained from a fingerstick, or from venipuncture, or an arterial blood sample), a urine sample, a biopsy sample, a tissue slice, stool sample, or other biological sample; a water sample, a soil sample, a food sample, an air sample; or other sample. A blood sample may comprise, e.g., whole blood, plasma, or serum. An automatic sample analysis device may receive a sample from the subject through a housing of the device. The sample collection may occur at a sample collection site, or elsewhere. The sample may be provided to the device at a sample collection site.

In some embodiments, an automatic sample analysis device may be configured to accept or hold a cartridge. In some embodiments, an automatic sample analysis device may comprise a cartridge. The cartridge may be removable from the automatic sample analysis device. In some embodiments, a sample may be provided to the cartridge of the automatic sample analysis device. Alternatively, a sample may be provided to another portion of an automatic sample analysis device. The cartridge and/or device may comprise a sample collection unit that may be configured to accept a sample.

A cartridge may include a sample, and may include reagents for use in processing or testing a sample, disposables for use in processing or testing a sample, or other materials. Following placement of a cartridge on, or insertion of a cartridge into, an automatic sample analysis device, one or more components of the cartridge may be brought into fluid communication with other components of the automatic sample analysis device. For example, if a sample is collected at a cartridge, the sample may be transferred to other portions of the automatic sample analysis device. Similarly, if one or more reagents are provided on a cartridge, the reagents may be transferred to other portions of the automatic sample analysis device, or other components of the automatic sample analysis device may be brought to the reagents. In some embodiments, the reagents or components of a cartridge may remain on-board the cartridge. In some embodiments, no fluidics are included that require tubing or that require maintenance (e.g., manual or automated maintenance).

A sample or reagent may be transferred to a device, such as an automatic sample analysis device. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a sample handling system (e.g., a pipette); for example, a sample, reagent, or aliquot thereof may be aspirated into an open-tipped transfer component, such as a pipette tip, which may be operably connected to a sample handling system which transfers the tip, with the sample, reagent, or aliquot thereof contained within the tip, to a location on or within the automatic sample analysis device. The sample, reagent, or aliquot thereof can be deposited at a location on or within the automatic sample analysis device. Sample and reagent, or multiple reagents, may be mixed using a sample handling system in a similar manner. One or more components of the cartridge may be transferred in an automated fashion to other portions of the automatic sample analysis device, and vice versa.

A device, such as an automatic sample analysis device, may have a fluid handling system. A fluid handling system may perform, or may aid in performing, transport, dilution, extraction, aliquotting, mixing, and other actions with a fluid, such as a sample. In some embodiments, a fluid handling system may be contained within a device housing. A fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component. The fluid handling system may have portion with an interior surface and an exterior surface and an open end. The fluid handling system may comprise a pipette, which may include a pipette body and a pipette nozzle, and may comprise a pipette tip. A pipette tip may or may not be removable from a pipette nozzle. In embodiments, a fluid handling system may use a pipette mated with a pipette tip; a pipette tip may be disposable. A tip may form a fluid-tight seal when mated with a pipette. A pipette tip may be used once, twice, or more times. In embodiments, a fluid handling system may use a pipette or similar device, with or without a pipette tip, to aspirate, dispense, mix, transport, or otherwise handle the fluid. The fluid may be dispensed from the fluid handling system when desired. The fluid may be contained within a pipette tip prior to being dispensed, e.g., from an orifice in the pipette tip. In embodiments, or instances during use, all of the fluid may be dispensed; in other embodiments, or instances during use, a portion of the fluid within a tip may be dispensed. A pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are in non-liquid form. A pipette tip may also facilitate mixture by metered delivery of multiple fluids simultaneously or in sequence, such as in 2-part substrate reactions.

The fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from one fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units. A base or support may connect one or more pipettes of the fluid handling system to one another.

An automatic sample analysis device may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. An automatic sample analysis device may be configured to perform one or more sample preparation action or step on the sample. Optionally, a sample may be prepared for a chemical reaction and/or physical processing step. A sample preparation action or step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads, processing with nanoparticles, or other sample preparation action or steps. For example, sample preparation may include one or more step to separate blood into serum and/or particulate fractions, or to separate any other sample into various components. Sample preparation may include one or more step to dilute and/or concentrate a sample, such as a blood sample, or other biological samples. Sample preparation may include adding an anti-coagulant or other ingredients to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

An automatic sample analysis device may be configured to run one or more assay on a sample, and to obtain data from the sample. An assay may include one or more physical or chemical treatments, and may include running one or more chemical or physical reactions. An automatic sample analysis device may be configured to perform one, two or more assays on a small sample of bodily fluid. One or more chemical reaction may take place on a sample having a volume, as described elsewhere herein. For example one or more chemical reaction may take place in a pill having less than femtoliter volumes. In an instance, the sample collection unit is configured to receive a volume of the bodily fluid sample equivalent to a single drop or less of blood or interstitial fluid. In embodiments, the volume of a sample may be a small volume, where a small volume may be a volume that is less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. In embodiments, all sample assay actions or steps are performed on a single sample. In embodiments, all sample assay actions or steps are performed by a single device. In embodiments, all sample assay actions or steps are performed within a housing of a single device. In embodiments, most sample assay actions or steps are performed by a single device, and may be performed within a housing of a single device. In embodiments, many sample assay actions or steps are performed by a single device, and may be performed within a housing of a single device. In embodiments, sample processing, preparation, or assay actions or steps may be performed by more than one device.

An automatic sample analysis device may be configured to perform a plurality of assays on a sample. In embodiments, an automatic sample analysis device may be configured to perform a plurality of assays on a single sample. In embodiments, an automatic sample analysis device may be configured to perform a plurality of assays on a single sample, where the sample is a small sample. For example, a small sample may have a sample volume that is a small volume of less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. An automatic sample analysis device may be capable of performing multiplexed assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, all sample assay actions or steps are performed by a single device. In embodiments, all of a plurality of assay actions or steps are performed within a housing of a single device. In embodiments, most sample assay actions or steps, of a plurality of assays, are performed by a single device, and may be performed within a housing of a single device. In embodiments, many sample assay actions or steps, of a plurality of assays, are performed by a single device, and may be performed within a housing of a single device. In embodiments, sample processing, preparation, or assay actions or steps may be performed by more than one device.

In embodiments, all of a plurality of assays may be performed in a short time period. In embodiments, such a short time period comprises less than about three hours, or less than about two hours, or less than about one hour, or less than about 40 minutes, or less than about 30 minutes, or less than about 25 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute, or other short time period.

An automatic sample analysis device may perform nucleic acid assays, including isothermal nucleic acid assays (e.g., assays for detecting and measuring nucleic acid targets in a sample, including DNA and RNA targets). In embodiments, an automatic sample analysis device may perform nucleic acid assays as disclosed in U.S. patent application Ser. No. 14/183,503, filed Feb. 18, 2014; U.S. patent application Ser. No. 14/214,850, filed Mar. 15, 2014; International Patent Application PCT/US2014/030034, filed Mar. 15, 2014; and in International Patent Application PCT/US2014/056151, filed Sep. 17, 2014. An automatic sample analysis device may perform antibody assays, including enzyme-linked immunosorbent assays (ELISA), and other assays for detecting and measuring the amounts of proteins (including antibodies), peptides, and small molecules in samples. An automatic sample analysis device may perform general chemistry assays, including electrolyte assays (e.g., assays for detecting and measuring the amounts of electrolytes such as sodium and potassium in a sample).

An automatic sample analysis device may be configured to detect one or more signals relating to the sample. An automatic sample analysis device may be configured to identify one or more properties of the sample. For instance, the automatic sample analysis device may be configured to detect the presence or concentration of one analyte or a plurality of analytes or a disease condition in the sample (e.g., in or through a bodily fluid, secretion, tissue, or other sample). Alternatively, the automatic sample analysis device may be configured to detect a signal or signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A chemical reaction or other processing step may be performed, with or without the sample. Examples of steps, tests, or assays that may be prepared or run by the device may include, but are not limited to immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation action or steps, or combinations thereof. Steps, tests, or assays that may be prepared or run by the device may include imaging, including microscopy, cytometry, and other techniques preparing or utilizing images. Steps, tests, or assays that may be prepared or run by the device may further include an assessment of histology, morphology, kinematics, dynamics, and/or state of a sample, which may include such assessment for cells.

A device may be capable of performing all on-board steps (e.g., steps or actions performed by a single device) in a short amount of time. A device may be capable of performing all on-board steps on a single sample in a short amount of time. For example, from sample collection from a subject to transmitting data and/or to analysis may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. The amount of time from accepting a sample within the device to transmitting data and/or to analysis from the device regarding such a sample may depend on the type or number of steps, tests, or assays performed on the sample. The amount of time from accepting a sample within the device to transmitting data and/or to analysis from the device regarding such a sample may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

A device may be configured to prepare a sample for disposal, or to dispose of a sample, such as a biological sample, following processing or assaying of a sample.

In embodiments, an automatic sample analysis device may be configured to transmit data obtained from a sample. In embodiments, an automatic sample analysis device may be configured to communicate over a network. An automatic sample analysis device may include a communication module that may interface with the network. An automatic sample analysis device may be connected to the network via a wired connection or wirelessly. The network may be a local area network (LAN) or a wide area network (WAN) such as the Internet. In some embodiments, the network may be a personal area network. The network may include the cloud. The automatic sample analysis device may be connected to the network without requiring an intermediary device, or an intermediary device may be required to connect an automatic sample analysis device to a network. An automatic sample analysis device may communicate over a network with another device, which may be any type of networked device, including but not limited to a personal computer, server computer, or laptop computer; personal digital assistants (PDAs) such as a Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Such communication may include providing data to a cloud computing infrastructure or any other type of data storage infrastructure which may be accessed by other devices.

An automatic sample analysis device may provide data regarding a sample to, e.g., a health care professional, a health care professional location, such as a laboratory, or an affiliate thereof. One or more of a laboratory, health care professional, or subject may have a network device able to receive or access data provided by the automatic sample analysis device. An automatic sample analysis device may be configured to provide data regarding a sample to a database. An automatic sample analysis device may be configured to provide data regarding a sample to an electronic medical records system, to a laboratory information system, to a laboratory automation system, or other system or software. An automatic sample analysis device may provide data in the form of a report.

A laboratory, device, or other entity or software may perform analysis on data regarding a sample in real-time. A software system may perform chemical analysis and/or pathological analysis, or these could be distributed amongst combinations of lab, clinical, and specialty or expert personnel. Analysis may include qualitative and/or quantitative evaluation of a sample. Data analysis may include a subsequent qualitative and/or quantitative evaluation of a sample. Optionally, a report may be generated based on raw data, pre-processed data, or analyzed data. Such a report may be prepared so as to maintain confidentiality of the data obtained from the sample, the identity and other information regarding the subject from whom a sample was obtained, analysis of the data, and other confidential information. The report and/or the data may be transmitted to a health care professional. Data obtained by an automatic sample analysis device, or analysis of such data, or reports, may be provided to a database, an electronic medical records system, to a laboratory information system (LIS), to a laboratory automation system (LAS), or other system or software.

Description and disclosure of examples of reagents, assays, methods, kits, devices, and systems which may use, or be used with, methods, devices, and systems disclosed herein may be found, for example, in U.S. Pat. No. 8,088, 593; U.S. Pat. No. 8,380,541; U.S. Pat. No. 8,435,738; U.S. Pat. No. 8,475,739; U.S. Pat. No. 8,840,838; U.S. patent application Ser. No. 14/183,503, filed Feb. 18, 2014; U.S. patent application Ser. No. 13/933,035, filed Jul. 1, 2013; U.S. patent application Ser. No. 13/769,820, filed Feb. 18, 2013; U.S. patent application Ser. No. 14/183,503, filed Feb. 18, 2014; patent application Ser. No. 14/214,850, filed Mar. 15, 2014; International Patent Application PCT/US2014/030034, filed Mar. 15, 2014; International Patent Application PCT/US2014/056151, filed Sep. 17, 2014; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. application Ser. No. 13/945,202, filed Jul. 18, 2013, the disclosures of which patents and patent applications are all hereby incorporated by reference in their entireties.

Systems and Devices Suitable for Mixing Fluids

The Figures and discussion regarding the figures provide further description and disclosure of the methods for mixing fluids, devices suitable for use in the practice of these methods, and systems for mixing fluids according to the methods disclosed herein.

FIG. 1 is a schematic, partly perspective view showing a system 100 having features as disclosed herein. System 100 includes a mixing vessel 102 with an inner surface 104 defining an interior cavity 106. A pipette tip 108 having an orifice 110 at the end of distal portion 112 is shown disposed partially within the interior cavity 106 of the mixing vessel 102. The pipette tip 108 has an interior cavity 114 and a proximal end 116 which is engaged with a nozzle 118 of a head 120. A head 120 may include mechanical and structural components associated with a nozzle 118. A nozzle 118 is configured to engage, and to hold, a pipette tip 108; as shown, nozzle 118 engages with distal portion 116 of the pipette tip 108. The head 120 and nozzle 118 are configured to provide pressure to the interior cavity 114 of pipette tip 108. These elements are shown in cross-sectional schematic view.

In a partial perspective view, the head 120 is shown attached to a base 122; another head 120 and nozzle 118 are shown attached to base 122 in the partial perspective view. A base 122 may have one, two, or more heads 120 and nozzles 118.

As shown in cross-sectional schematic view, base 122 is connected to a fluid handling apparatus 124; such a fluid handling apparatus 124 may include mechanical elements (e.g., a gantries, motors, gears, chains, belts, rollers, slides, and other mechanical elements which move, and which control the movements and position of, a head 120 and nozzle 118, and pipette tips 108 attached to a nozzle 118. In embodiments, a fluid handling apparatus 124 is configured to move a pipette tip 108 attached to a nozzle 118 and head 120 to a proper position for use in mixing fluids. Such pipette movements may include horizontal movements to any position in a plane; vertical movements; angular (e.g., tilting) movements; rotation movements; and combinations thereof, and any other movements needed to place a pipette tip 108 in a proper position for mixing fluids in a mixing vessel 102.

A system 100, including in embodiments a fluid handling apparatus 124, may also include hydraulic elements, including pumps, tubing, valves, and other elements for providing and directing fluids to desired locations. For example, a system 100 as shown in FIG. 1 includes a reservoir 126, which is operably connected to head 120 and nozzle 118 by conduit 132 effective to provide fluid to the interior 114 of pipette tip 108. In addition, a system 100 as shown in FIG. 1 includes a pressure source 128, which is operably connected to reservoir 126 by a connection 13; the pressure source 128, via connection 130 to reservoir 126 and conduit 132 may serve as a source of pressure (positive or negative) to head 120 and nozzle 118 effective to provide pressure to the interior 114 of pipette tip 108. A pressure source may be, for example, a pump, a piston, a plunger, a tank containing pressurized gas or fluid under pressure, a tank containing vacuum or other low pressure fluid, or other source of pressure or suction).

A system 100 having a fluid handling apparatus 124 may further include a processor 134; a processor 134 may be connected to a fluid handling apparatus 124 by a communication link 136. In embodiments, a processor 134 may, at least in part, control the operation and movements of a fluid handling apparatus 124. A communication link 136 may be a one-way link (e.g., providing only input to the system 100 or to the fluid handling apparatus 124, or providing only output from the system 100 or from the fluid handling apparatus 124), or may be a two-way communication link (providing input to, and output from, the system 100 or to and from the fluid handling apparatus 124). A system 100 may interact with a computer network 138 (such as the "cloud"); in embodiments, a system 100 includes a computer network 138. A communication link 140 may connect a system 100, including a fluid handling apparatus 124, to a computer network 138. A communication link 140 may be a one-way link, or may be a two-way link.

A head 120 has at least one nozzle 118, where each nozzle 118 is configured to engage a pipette tip 108; a pipette tip 108 fits onto, and may be held by, a nozzle 118. A pipette tip 108 has a proximal end 116 configured to engage with a nozzle 118, and to provide a fluid pathway, via the nozzle 118, between the head 120 and the pipette tip 108. A pipette tip 108 has a distal end 112 with an orifice 110 from which fluid may exit or enter. When held by a nozzle 118, a pipette tip 108 may be sealed to a nozzle 118 effective that pressure or suction within the pipette tip 108 is effective to cause fluid flow into or out of the orifice 110 of the pipette tip 108, without dislodging the pipette tip 108 from the nozzle 118. A base 122 may be movable with respect to (e.g., within) an automatic sample analysis device or system. A head 120 may be movable with respect to a base 122 to which it is operably connected. A nozzle 118 may be movable with respect to a base 122, or to a head 120, or both, to which it is operably connected. Movement of a base 122, a head 120, a nozzle 118, or combinations of these, may be used to position a pipette tip 108 to any desired location within an automatic sample analysis device or system.

Systems 100 as illustrated in FIG. 1 may use pipette tips 108 and mixing vessels 102 to mix fluids, including to mix small volumes of fluids, according to the methods disclosed herein. Examples of methods of mixing fluids, including mixing small volumes of fluid, are provided in the following discussion with reference to the Figures.

FIGS. 2A, 2B, 2C, and 2D provide cross-sectional schematic views of a pipette tip 208 partially inserted within an interior cavity 206 of a mixing vessel 202. As shown, e.g., in FIG. 2A, pipette tip 208 has a distal portion 216; a proximal portion 212 with an orifice 210; and an internal cavity 214. The mixing vessel 202 has an internal surface 204 defining an interior cavity 206. A small volume of a first fluid 250 is present in the interior cavity 206 within the mixing vessel 202, and a small volume of a second fluid 252 is present within the internal cavity 214 of the pipette tip 208. Orifice 210 connects with internal cavity 214 of pipette tip 208. In embodiments, a tube or other hollow implement or element may be used in place of the pipette.

Figure 2A:
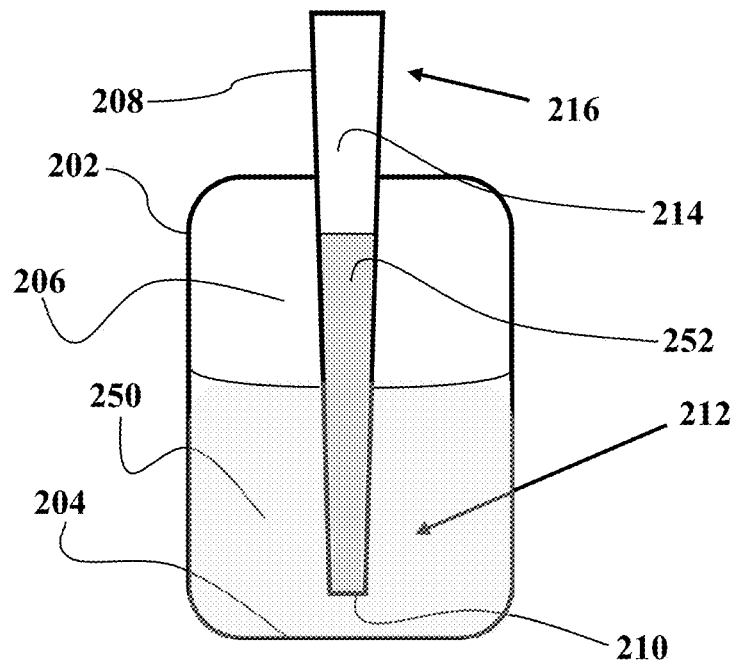
FIG. 2A shows a pipette tip inserted within an internal cavity of a mixing vessel, with fluid present within the mixing vessel and fluid within the pipette tip. In embodiments, a tube or other hollow implement or element may be used in place of the pipette.
Figure 2B:
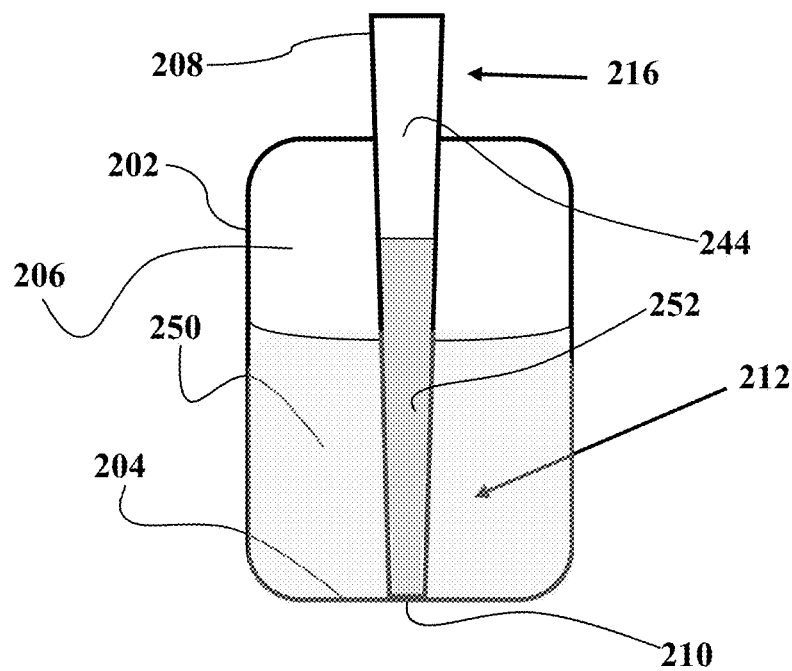
FIG. 2B shows the pipette tip containing a small volume of fluid of FIG. 2A pressing its tip against the internal wall of the internal cavity of the mixing vessel of FIG. 2A.

FIG. 2B shows the pipette tip 208 and mixing vessel 202 of FIG. 2A. The pipette tip 208 containing a small volume of fluid 252 is shown pressing its distal portion 212 against the internal surface 204 within the interior cavity 206 of the mixing vessel 202. Orifice 210 is occluded while it is pressed against the internal surface 204 within the interior cavity 206 of the mixing vessel 202. Occlusion of orifice 210 prevents fluid flow through orifice 210 into or out of internal cavity 214 of pipette tip 208.

Figure 2C:
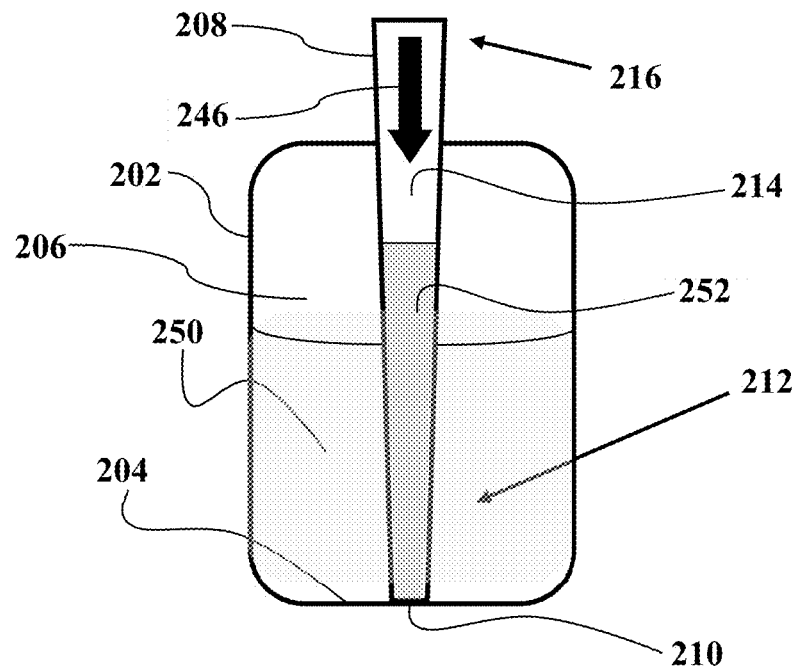
FIG. 2C shows the pipette of FIGS. 2A and 2B with its tip pressed against the internal wall of the internal cavity of the mixing vessel, and with increased internal pressure within the tip. Note that no fluid flows from the pipette into the mixing vessel while the tip is pressed against the interior wall of the mixing vessel despite the pressure.

FIG. 2C shows the pipette tip 208 and mixing vessel 202 of FIGS. 2A and 2B during application of pressure 246 within the internal cavity 214 of pipette tip 208. The pipette tip 208 of FIGS. 2A and 2B with its orifice 210 pressed against the internal surface 204 of the interior cavity 206 of the mixing vessel 202, and with increased internal pressure (indicated by arrow 246) within the pipette tip 208. Orifice 210 remains pressed against the internal surface 204 within the interior cavity 206 of the mixing vessel 202, and remains occluded. Note that no fluid flows from the pipette tip 208 into the mixing vessel 202 while the pipette tip 208 is pressed against the internal surface 204 of the mixing vessel 202 despite the pressure 246.

Figure 2D:
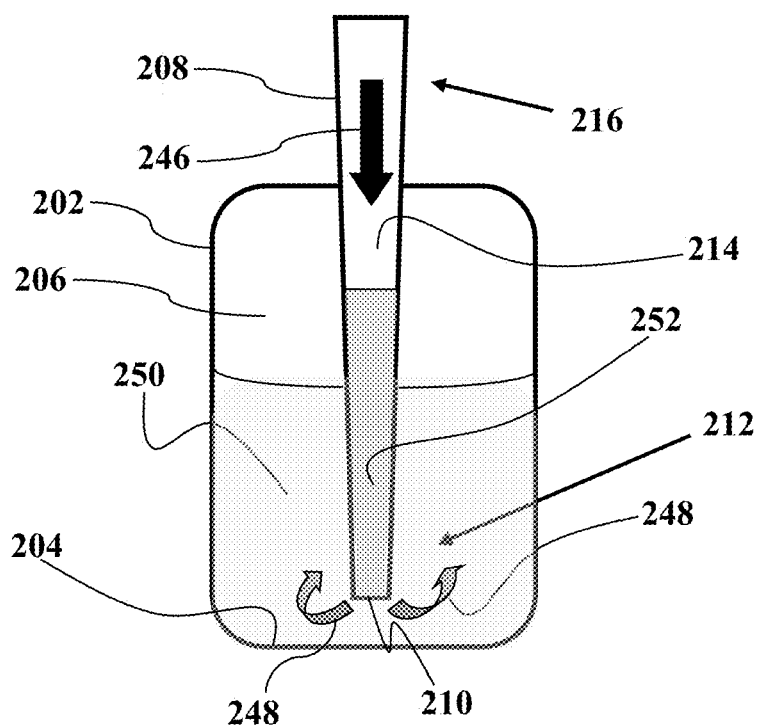
FIG. 2D shows the pipette of FIGS. 2A, 2B, and 2C, still with increased pressure within the pipette, and with its tip removed and retracted away from the internal wall of the internal cavity of the mixing vessel, removing the occlusion of the tip. Note that fluid flows freely from the pipette into the mixing vessel. Such fluid flow is greater, of greater force, and of greater velocity than the flow would be had there been no occlusion during the prior application of pressure; such greater flow, greater force, and greater velocity improve mixing of fluids within the mixing vessel.

FIG. 2D shows the pipette tip 208 and mixing vessel 202 of FIGS. 2A, 2B, and 2C, still with increased pressure 246 within the pipette tip 208, and with the pipette tip 208 retracted away from the internal surface 204 of the mixing vessel 202, removing the occlusion of the orifice 210. As indicated by the arrows 248, fluid flows freely from the pipette tip 208 into the mixing vessel 208. Such fluid flow is greater, of greater force, and of greater velocity than the flow would be had there been no occlusion during the prior application of pressure; such greater flow, greater force, and greater velocity improve the mixing of fluids within the mixing vessel 202.

FIGS. 3A, 3B, 3C, and 3D provide cross-sectional schematic views of a pipette tip 308 partially inserted within an internal cavity 306 of a mixing vessel 302. As shown, e.g., in FIG. 3A, pipette tip 308 has a distal portion 316; a proximal portion 312 with an orifice 310; and an internal cavity 314. Orifice 310 connects with internal cavity 314 of pipette tip 308. The mixing vessel 302 has an internal surface 304 defining interior cavity 306. A small volume of a first fluid 342 is present in the interior cavity 306 within the mixing vessel 302, and a small volume of a second fluid 350 is present within the interior cavity 314 of the pipette tip 308. In embodiments, a tube or other hollow implement or element may be used in place of the pipette.

Figure 3A:
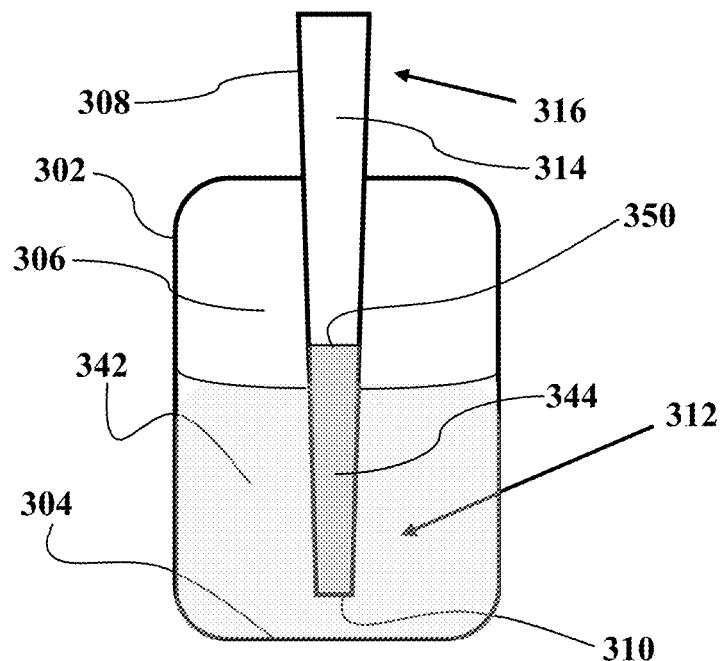
FIG. 3A shows a pipette tip inserted within an internal cavity of a mixing vessel, with fluid present within the mixing vessel and fluid within the pipette tip. In embodiments, a tube or other hollow implement or element may be used in place of the pipette.
Figure 3B:
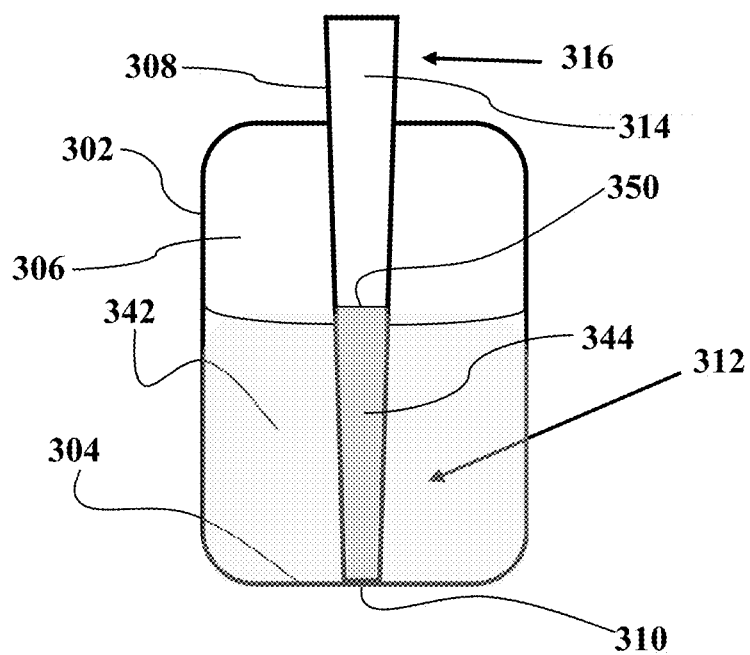
FIG. 3B shows the pipette tip containing a small volume of fluid of FIG. 3A pressing its tip against the internal wall of the internal cavity of the mixing vessel of FIG. 3A.

FIG. 3B shows the pipette tip 308 and mixing vessel 302 of FIG. 3A. The pipette tip 308 containing a small volume of fluid 344 is shown pressing its distal portion 312 against the internal surface 304 within the interior cavity 306 of the mixing vessel 302. Orifice 310 is occluded while it is pressed against the internal surface 304 within the interior cavity 306 of the mixing vessel 302. Occlusion of orifice 310 prevents fluid flow through orifice 310 into or out of internal cavity 314 of pipette tip 308.

Figure 3C:
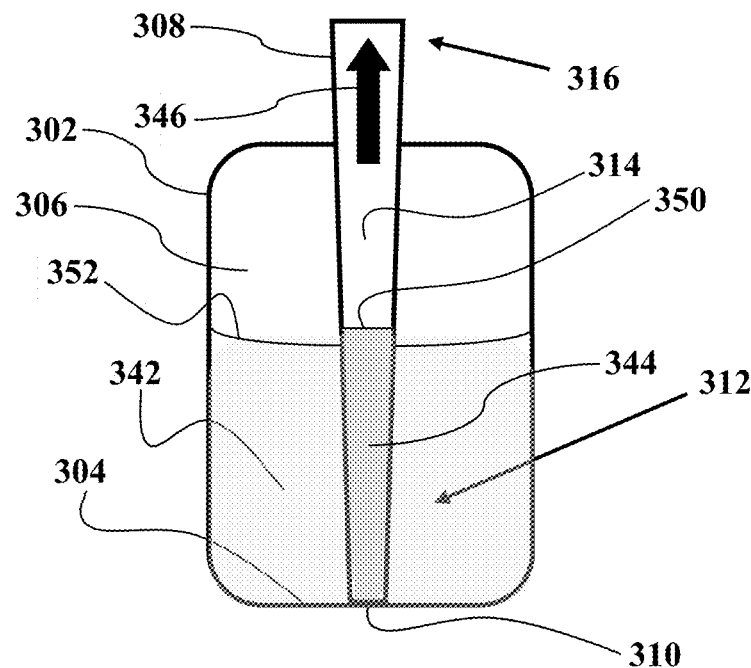
FIG. 3C shows the pipette of FIGS. 3A and 3B with its tip pressed against the internal wall of the internal cavity of the mixing vessel, and with decreased internal pressure (suction) within the tip. Note that no fluid flows from the pipette into the mixing vessel while the tip is pressed against the interior wall of the mixing vessel despite the suction.

FIG. 3C shows the pipette tip 308 and mixing vessel 302 of FIGS. 3A and 3B during application of pressure 346 within the internal cavity 314 of pipette tip 308. The pipette tip 308 is shown with its orifice 310 pressed against the internal surface 304 of the interior cavity 306 of the mixing vessel 302, with decreased internal pressure (suction; shown by arrow 346) within the internal cavity 314 of pipette tip 308. Orifice 310 remains pressed against the internal surface 304 within the interior cavity 306 of the mixing vessel 302, and remains occluded. Note that, despite the suction 346, no fluid flows from the pipette tip 308 from the mixing vessel 302 while orifice 310 remains occluded while the pipette tip 308 is pressed against the internal surface 304 of the mixing vessel 302.

Figure 3D:
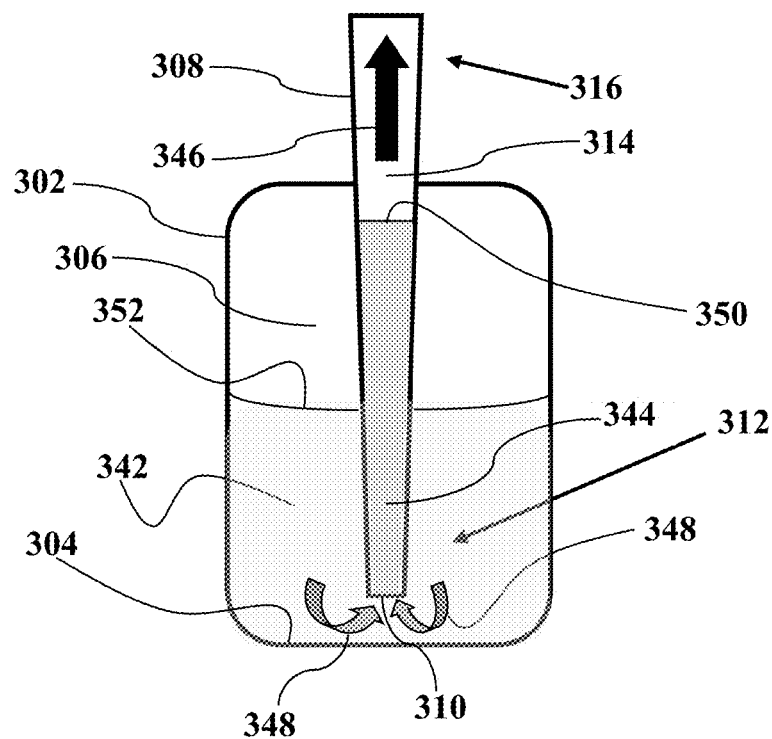
FIG. 3D shows the pipette of FIGS. 3A, 3B, and 3C, still with decreased pressure within the pipette, and with its tip removed and retracted away from the internal wall of the internal cavity of the mixing vessel, removing the occlusion of the tip. Note that fluid flows freely from the mixing vessel into the pipette, providing fluid flow within the mixing vessel as well as into the pipette. Such fluid flow is greater, of greater force, and of greater velocity than the flow would be had there been no occlusion during the prior application of pressure; such greater flow, greater force, and greater velocity improve mixing of fluids within the pipette and mixing vessel.

FIG. 3D shows the pipette tip 308 and mixing vessel 302 of FIGS. 3A, 3B, and 3C, still with decreased pressure (suction) 346 within the pipette tip 308, and with the pipette tip 308 retracted away from the internal surface 304 of the mixing vessel 302, removing the occlusion of the orifice 310. As indicated by the arrows 348, fluid flows freely into the pipette tip 308 from the mixing vessel 302. Such fluid flow is greater, of greater force, and of greater velocity than the flow would be had there been no occlusion during the prior application of pressure; such greater flow, greater force, and greater velocity improve the mixing of fluids, including mixing of fluids within the mixing vessel 302.

Figure 4A:
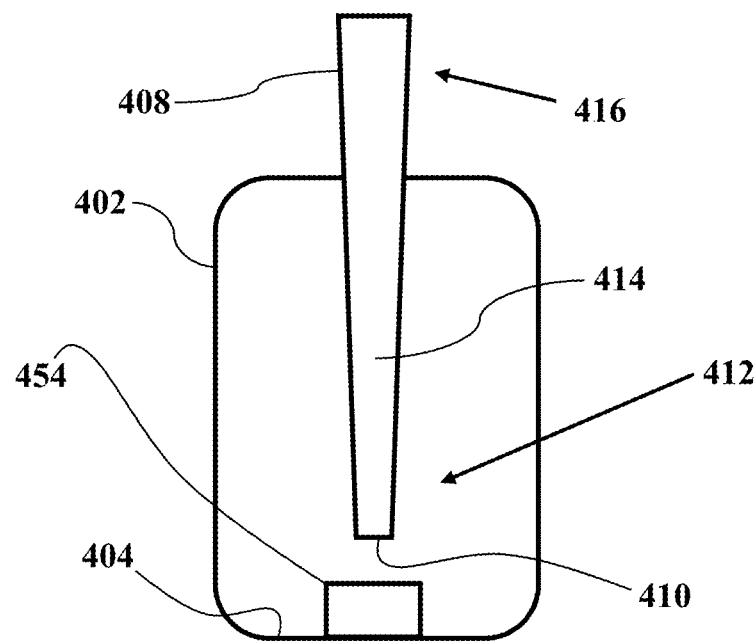
FIG. 4A provides a schematic cross-sectional illustration of a pipette tip within a mixing vessel, where the mixing vessel has a raised feature on its inner surface, the raised feature being configured to engage the pipette tip and to occlude the orifice of the pipette tip. In this figure, the pipette tip is not engaged with the raised feature on the inner surface of the mixing vessel, and the orifice of the pipette tip is not occluded.

FIG. 4A provides a schematic cross-sectional illustration of a pipette tip 408 placed partially within a mixing vessel 402, the pipette tip 408 having a proximal portion 416, an inner cavity 414 connected with an orifice 410, the orifice situated on the distal portion 412 of the pipette tip 408. The mixing vessel 402 has a raised feature 454 on its inner surface 404, the raised feature 454 being configured to engage the pipette tip 408 and to occlude the orifice 410 of the pipette tip 408. Pipette tip 408 has a proximal portion 416, and an internal cavity 414 connecting with an orifice 410 in its distal portion 412. In this figure, the pipette tip 408 is not engaged with the raised feature 454 on the inner surface 404 of the mixing vessel 402, and the orifice 410 of the pipette tip 408 is not occluded.

Figure 4B:
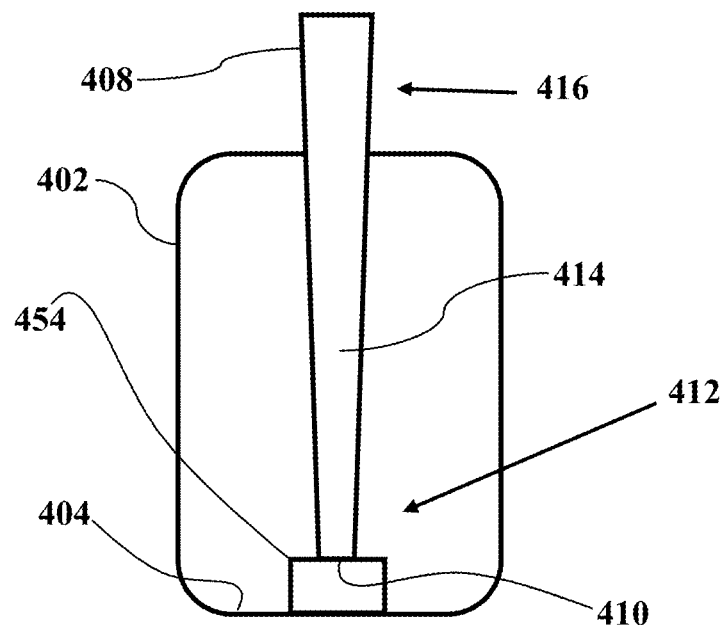
FIG. 4B provides a schematic cross-sectional illustration of the pipette tip and mixing vessel as shown in FIG. 4A. In this figure, the pipette tip is engaged with the raised feature on the inner surface of the mixing vessel, and the orifice of the pipette tip is occluded.

FIG. 4B provides a schematic cross-sectional illustration of the pipette tip 408 and mixing vessel 402 as shown in FIG. 4A. In this figure, the pipette tip 408 is engaged with the raised feature 454 on the inner surface 404 of the mixing vessel 402, and the orifice 410 of the pipette tip 408 is occluded. Occlusion of orifice 410 prevents fluid flow through orifice 410 into or out of internal cavity 414 of pipette tip 408. Application of pressure within internal cavity 414 of pipette tip 408 while orifice 410 remains occluded is effective to provide pressure build-up (whether positive or negative) within internal cavity 414, and to provide increased fluid flow through orifice 410 upon release of the occlusion of orifice 410.

Figure 4C:
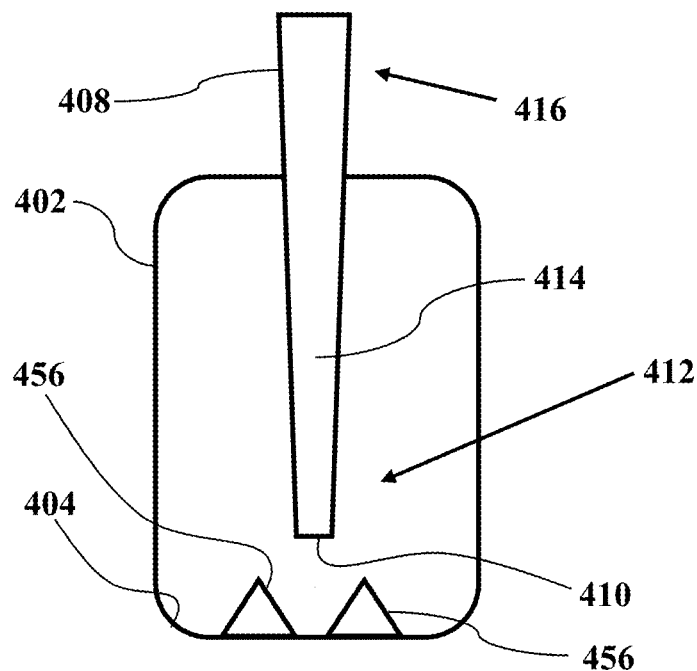
FIG. 4C provides a schematic cross-sectional illustration of a pipette tip within a mixing vessel, where the inner surface of the mixing vessel has a raised feature having angled surfaces configured to engage the pipette tip and to occlude the orifice of the pipette tip. In this figure, the pipette tip is not engaged with the raised feature on the inner surface of the mixing vessel, and the orifice of the pipette tip is not occluded.

FIG. 4C provides a schematic cross-sectional illustration of a pipette tip 408 positioned at least partly within a mixing vessel 402, the pipette tip 408 having a proximal portion 416, an inner cavity 414 connected with an orifice 410, the orifice situated on the distal portion 412 of the pipette tip 408. The inner surface 404 of the mixing vessel 402 has a raised feature 456 (shown in cross-section; this schematic illustration of raised feature 456 is meant to indicate that raised feature 456 is an annular feature with angled surfaces providing a beveled depression into which distal portion 412 of pipette tip 408 may be pressed). Raised feature 456 is configured to engage distal portion 412 of pipette tip 408 and to occlude the orifice 410 of the pipette tip 408. In this figure, the pipette tip 408 is not engaged with the raised feature 456 on the inner surface 404 of the mixing vessel 402, and the orifice 410 of the pipette tip 408 is not occluded.

Figure 4D:
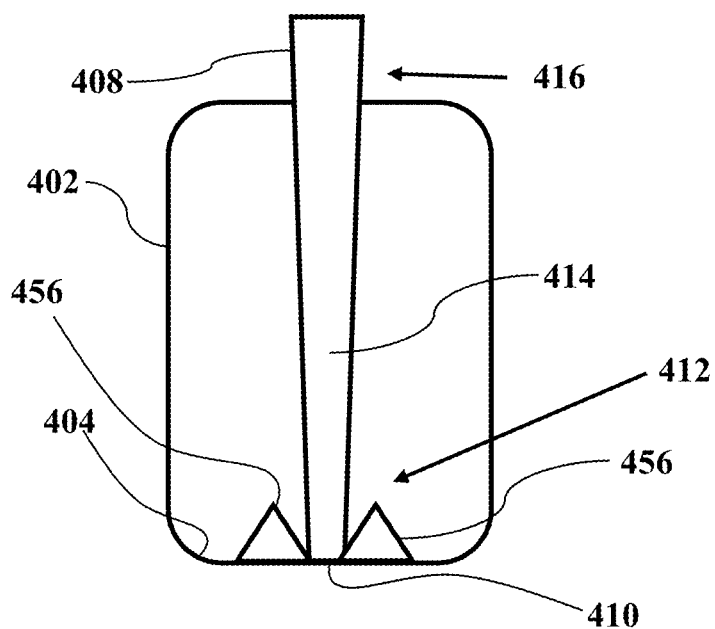
FIG. 4D provides a schematic cross-sectional illustration of the pipette tip and mixing vessel as shown in FIG. 4C. In this figure, the pipette tip is engaged with the raised feature having angled surfaces, and the orifice of the pipette tip is occluded.

FIG. 4D provides a schematic cross-sectional illustration of the pipette tip 408 and mixing vessel 402 as shown in FIG. 4C. In this figure, the distal portion 412 of pipette tip 408 is engaged with the raised feature 456, and the orifice 410 of the pipette tip 408 is occluded. The angled surfaces of raised feature 456 press laterally on distal portion 412 of pipette tip 408 as pipette tip 408 is pressed against the inner surface 404 of the mixing vessel 402, effecting and enhancing the occlusion of orifice 410. Occlusion of orifice 410 prevents fluid flow through orifice 410 into or out of internal cavity 414 of pipette tip 408. Application of pressure within internal cavity 414 of pipette tip 408 while orifice 410 remains occluded is effective to provide pressure build-up (whether positive or negative) within internal cavity 414, and to provide increased fluid flow through orifice 410 upon release of the occlusion of orifice 410.

Figure 5A:
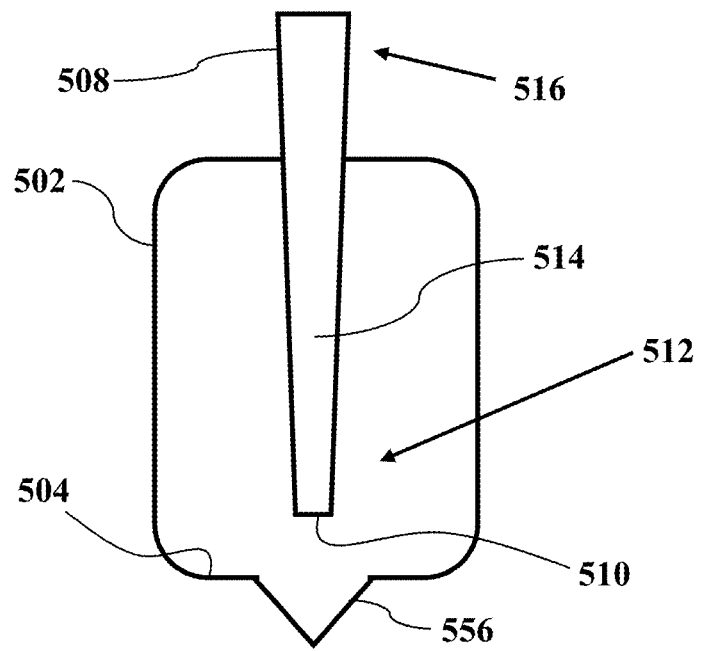
FIG. 5A provides a schematic cross-sectional illustration of a pipette tip within a mixing vessel, where the mixing vessel has a feature with angled surfaces indented in its inner surface, the indented feature being configured to engage the pipette tip and to occlude the orifice of the pipette tip. In this figure, the pipette tip is not engaged with the feature indented in the inner surface of the mixing vessel, and the orifice of the pipette tip is not occluded.

FIG. 5A provides a schematic cross-sectional illustration of a pipette tip 508 placed partially within a mixing vessel 502, pipette tip 508 having a proximal portion 516, a distal portion 512, and an internal cavity 514 connected with an orifice 510 on the distal portion 512. The mixing vessel 502 has a feature 556 with angled surfaces indented in its inner surface 504, the indented feature 556 being configured to engage a distal portion 512 of pipette tip 508 and to occlude the orifice 510 of the pipette tip 508. In this figure, the pipette tip 508 is not engaged with the feature 556 indented in the inner surface 504 of the mixing vessel 502, and the orifice 510 of the pipette tip 508 is not occluded.

Figure 5B:
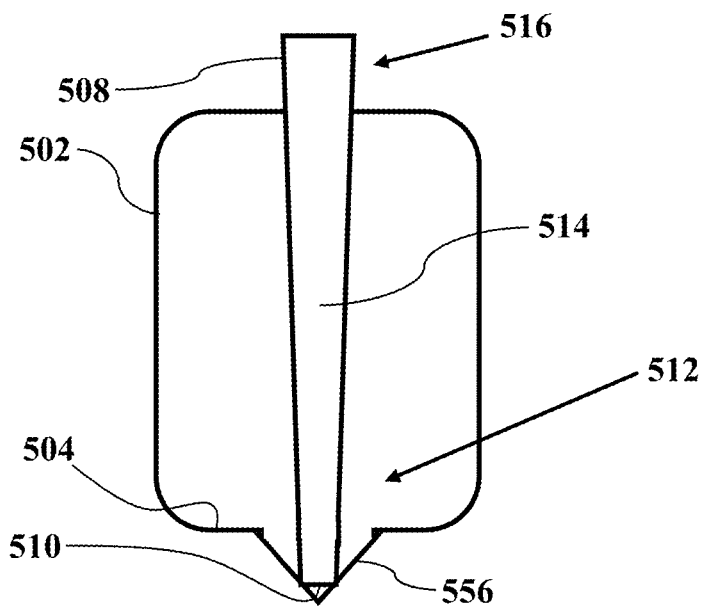
FIG. 5B provides a schematic cross-sectional illustration of the pipette tip and mixing vessel as shown in FIG. 5A. In this figure, the pipette tip is engaged with the feature with angled surfaces indented in the inner surface of the mixing vessel, and the orifice of the pipette tip is occluded.

FIG. 5B provides a schematic cross-sectional illustration of the pipette tip 508 and mixing vessel 502 as shown in FIG. 5A. In this figure, the pipette tip 508 is engaged with the feature 556 with angled surfaces indented in the inner surface 504 of the mixing vessel 502, and the orifice 510 of the pipette tip 508 is occluded. Application of pressure within internal cavity 514 of pipette tip 508 while orifice 510 remains occluded is effective to provide pressure build-up (whether positive or negative) within internal cavity 514, and to provide increased fluid flow through orifice 510 upon release of the occlusion of orifice 510. It will be understood that such an indented feature 556 need not be placed centrally on a bottom inner surface 504 of a mixing vessel 502; in embodiments, such a feature 556 may be eccentrically placed on a bottom inner surface 504 of a mixing vessel 502; may be placed, e.g., at or near an edge where a side wall and a bottom inner surface 504 of a mixing vessel 502 meet; or elsewhere at a position suitable for pressing a pipette tip 508 against effective to occlude the pipette tip 508.

Figure 5C:
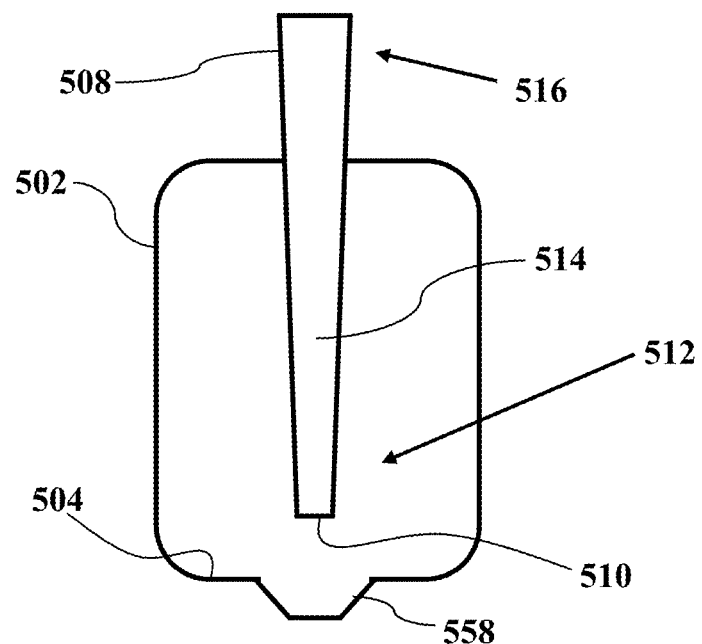
FIG. 5C provides a schematic cross-sectional illustration of a pipette tip within a mixing vessel, where the mixing vessel has a feature having angled surfaces and a flat bottom indented in the inner surface of the mixing vessel, the feature being configured to engage the pipette tip and to occlude the orifice of the pipette tip. In this figure, the pipette tip is not engaged with the indented feature on the inner surface of the mixing vessel, and the orifice of the pipette tip is not occluded.

FIG. 5C provides a schematic cross-sectional illustration of a pipette tip 508 disposed partly within a mixing vessel 502, pipette tip 508 having a proximal portion 516, a distal portion 512, and an internal cavity 514 connected with an orifice 510 on the distal portion 512. The mixing vessel 502 has a feature 558 having angled surfaces and a flat bottom indented in the inner surface 504 of the mixing vessel 502, the feature 558 being configured to engage the pipette tip 508 and to occlude the orifice 510 of the pipette tip 508. In this figure, the pipette tip 508 is not engaged with the indented feature 558 on the inner surface 504 of the mixing vessel 502, and the orifice 510 of the pipette tip 508 is not occluded.

Figure 5D:
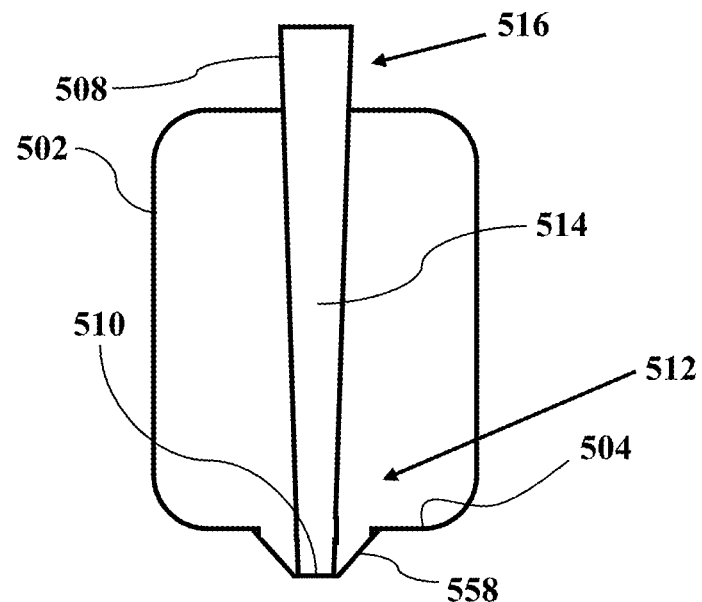
FIG. 5D provides a schematic cross-sectional illustration of the pipette tip and mixing vessel as shown in FIG. 5C. In this figure, the pipette tip is engaged with the indented feature having angled surfaces and a flat bottom, and the orifice of the pipette tip is occluded.

FIG. 5D provides a schematic cross-sectional illustration of the pipette tip 508 and mixing vessel 502 as shown in FIG. 5C. In this figure, the pipette tip 508 is engaged with the indented feature 558 having angled surfaces and a flat bottom, and the orifice 510 of the pipette tip 508 is occluded. Application of pressure within internal cavity 514 of pipette tip 508 while orifice 510 remains occluded is effective to provide pressure build-up (whether positive or negative) within internal cavity 514, and to provide increased fluid flow through orifice 510 upon release of the occlusion of orifice 510. It will be understood that such an indented feature 558 need not be placed centrally on a bottom inner surface 504 of a mixing vessel 502; in embodiments, such a feature 558 may be eccentrically placed on a bottom inner surface 504 of a mixing vessel 502; may be placed, e.g., at or near an edge where a side wall and a bottom inner surface 504 of a mixing vessel 502 meet; or elsewhere at a position suitable for pressing a pipette tip 508 against effective to occlude the pipette tip 508.

Figure 5E:
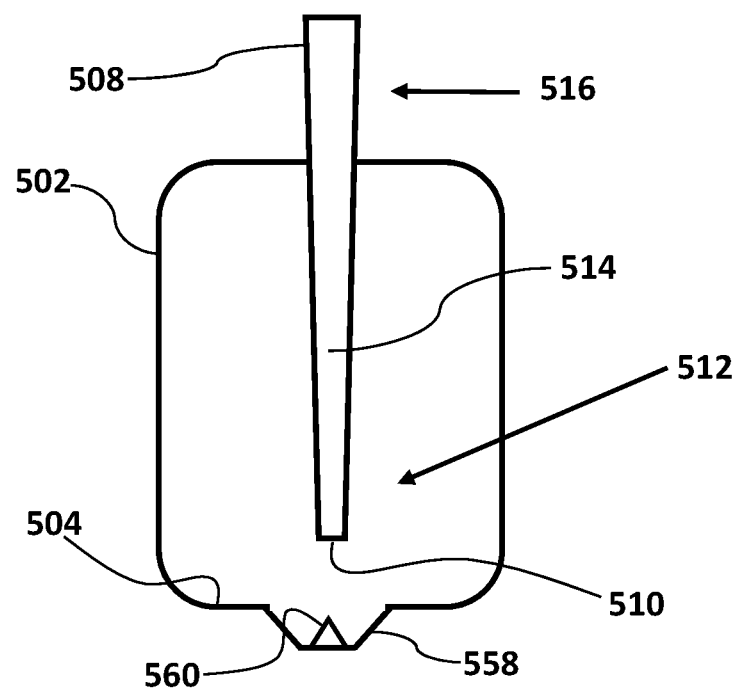
FIG. 5E provides a schematic cross-sectional illustration of a pipette tip within a mixing vessel, where the mixing vessel has a tapered indentation having angled surfaces indented in the inner surface of the mixing vessel, the tapered indentation further having a convex feature extending towards the interior cavity of the mixing vessel.

FIG. 5E provides a schematic cross-sectional illustration of a pipette tip within a mixing vessel, where the mixing vessel has an indented feature on the inner surface of the mixing vessel, the indented feature having a convex feature extending towards the interior cavity of the mixing vessel. In FIG. 5E, a pipette tip 508 is shown disposed partly within a mixing vessel 502, the pipette tip 508 having a proximal portion 516, a distal portion 512, and an internal cavity 514 connected with an orifice 510 on the distal portion 512. The mixing vessel 502 has an the inner surface 504 which includes angled surfaces 558 and a convex feature 560 extending towards the internal cavity 514 of the mixing vessel 502. The angled surfaces 558 and convex feature 560 are configured to engage the pipette tip 508 and to occlude the orifice 510 of the pipette tip 508. In this figure, the pipette tip 508 is not engaged with the angled surfaces 558 and convex feature 560 on the inner surface 504 of the mixing vessel 502, and the orifice 510 of the pipette tip 508 is not occluded. Downward movement of the pipette tip 508 places the orifice 510 in contact with the convex feature 560. Such contact between orifice 510 and convex feature 560 is effective to engage the pipette tip 508 with the convex feature 560 in order to occlude the orifice 510 of the pipette tip 508. The convex feature 560 is configured to extend at least partially into the orifice 510 of the pipette tip 508 effective to occlude the orifice 510 of the pipette tip 508 when the orifice 510 of the pipette tip 508 is placed in contact with the convex feature 560.

Figure 6A:
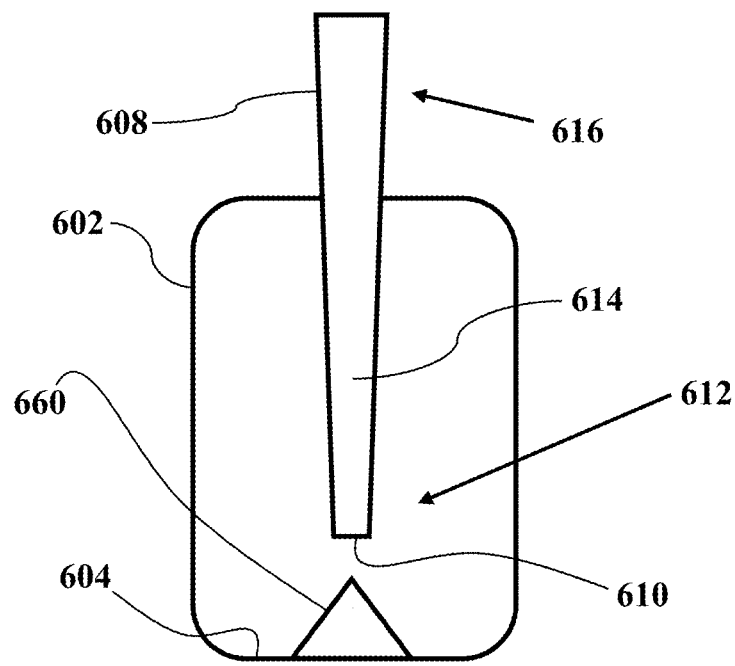
FIG. 6A provides a schematic cross-sectional illustration of a pipette tip within a mixing vessel, where the mixing vessel has a raised feature on its inner surface, the raised feature being configured to engage the pipette tip, including to enter at least partially into the pipette tip orifice, and to occlude the orifice. In this figure, the pipette tip is not engaged with the raised feature, and the orifice of the pipette tip is not occluded.

FIG. 6A provides a schematic cross-sectional illustration of a pipette tip 608 disposed partly within a mixing vessel 602, pipette tip 608 having a proximal portion 616, a distal portion 612, and an internal cavity 614 connected with an orifice 610 on the distal portion 612. The mixing vessel 602 has a raised feature 660 on its inner surface 604, the raised feature 660 being configured to engage the pipette tip 608, including to enter at least partially into the pipette tip orifice 610, and to occlude the orifice 610. In this figure, the pipette tip 608 is not engaged with the raised feature 660, and the orifice 610 of the pipette tip 608 is not occluded.

Figure 6B:
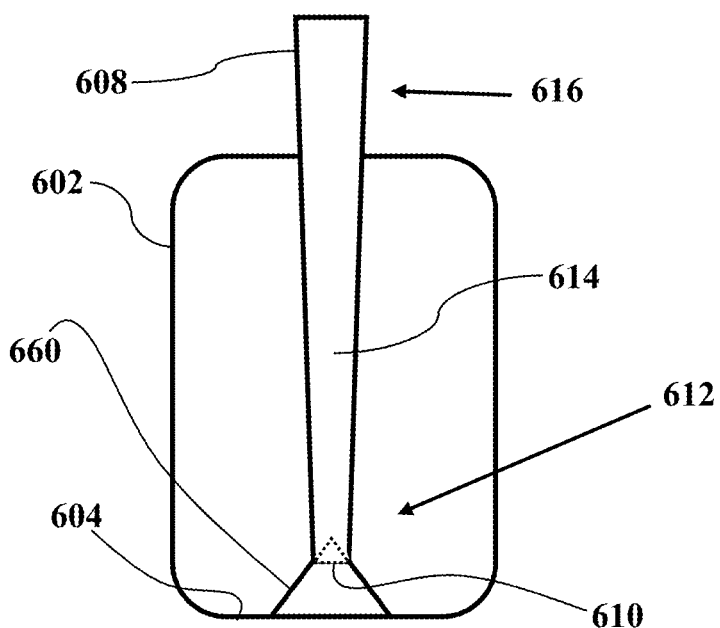
FIG. 6B provides a schematic cross-sectional illustration of the pipette tip and mixing vessel as shown in FIG. 6A. In this figure, the pipette tip is engaged with the raised feature on the inner surface of the mixing vessel, and the orifice of the pipette tip is occluded with part of the raised feature protruding into the pipette tip orifice.

FIG. 6B provides a schematic cross-sectional illustration of the pipette tip and mixing vessel as shown in FIG. 6A. In this figure, the pipette tip 608 is engaged with the raised feature 660 on the inner surface 604 of the mixing vessel 602, and the orifice 610 of the pipette tip 608 is occluded with part of the raised feature 660 protruding into the pipette tip orifice 610. Application of pressure within internal cavity 614 of pipette tip 608 while orifice 610 remains occluded is effective to provide pressure build-up (whether positive or negative) within internal cavity 614, and to provide increased fluid flow through orifice 610 upon release of the occlusion of orifice 610. It will be understood that such a raised feature 660 need not be placed centrally on a bottom inner surface 604 of a mixing vessel 602; in embodiments, such a feature 660 may be eccentrically placed on a bottom inner surface 604 of a mixing vessel 602; may be placed, e.g., at or near an edge where a side wall and a bottom inner surface 604 of a mixing vessel 602 meet; or elsewhere at a position suitable for pressing a pipette tip 608 against effective to occlude the pipette tip 608.

Figure 7A:
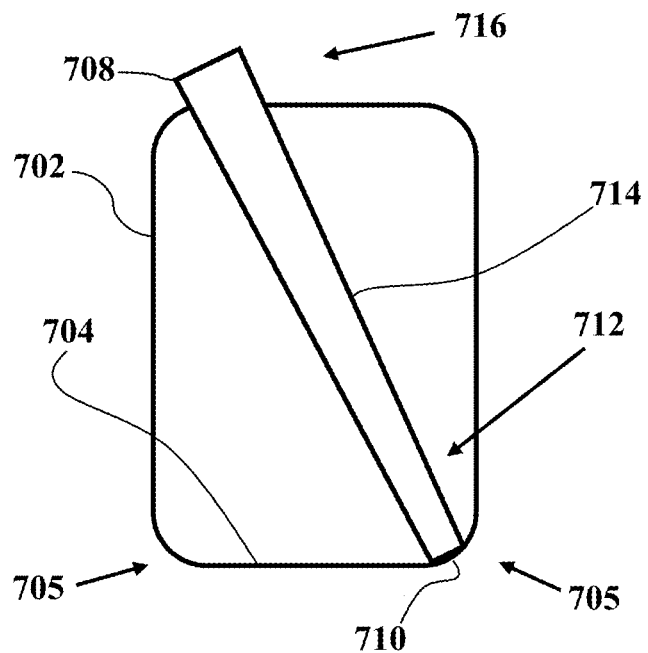
FIG. 7A provides a schematic cross-sectional illustration of a pipette tip within a mixing vessel, the mixing vessel having curved portions on its inner surface. In this figure, the pipette tip is engaged with the inner surface of the mixing vessel, and the orifice of the pipette tip is occluded by the engagement.

FIG. 7A provides a schematic cross-sectional illustration of a pipette tip 708 disposed partly within a mixing vessel 702, pipette tip 708 having a proximal portion 716, a distal portion 712, and an internal cavity 714 connected with an orifice 710 on the distal portion 712. The mixing vessel 702 has curved portions 705 on its inner surface 704. In this figure, the pipette tip 708 is engaged with a curved portion 705 of the inner surface 704 of the mixing vessel 702, and the orifice 710 of the pipette tip 708 is occluded by the engagement. Application of pressure within internal cavity 714 of pipette tip 708 while orifice 710 remains occluded is effective to provide pressure build-up (whether positive or negative) within internal cavity 714, and to provide increased fluid flow through orifice 710 upon release of the occlusion of orifice 710.

Figure 7B:
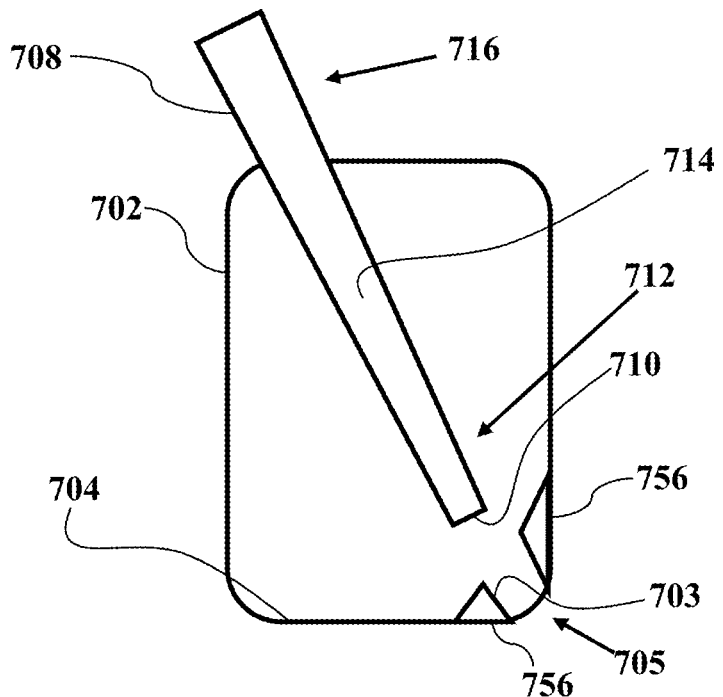
FIG. 7B provides a schematic cross-sectional illustration of a pipette tip within a mixing vessel, where the mixing vessel has a raised feature on its inner surface, the raised feature having angled surfaces and a curved bottom. The raised feature is configured to engage the pipette tip and to occlude the orifice. In this figure, the pipette tip is not engaged with the raised feature, and the orifice of the pipette tip is not occluded.

FIG. 7B provides a schematic cross-sectional illustration of a pipette tip 708 within a mixing vessel 702, pipette tip 708 having a proximal portion 716, a distal portion 712, and an internal cavity 714 connected with an orifice 710 on the distal portion 712. The mixing vessel 702 has a raised feature 756 on its inner surface, the raised feature 756 having angled surfaces 703 and a curved bottom 705. Raised feature 756 is shown in cross-section; this schematic illustration of raised feature 756 is meant to indicate that raised feature 756 is an annular feature with angled surfaces providing a beveled depression into which distal portion 712 of pipette tip 708 may be pressed. The raised feature 756 is configured to engage the pipette tip 708 and to occlude the orifice 710. In this figure, the pipette tip 708 is not engaged with the raised feature 756, and the orifice 710 of the pipette tip 708 is not occluded.

Figure 7C:
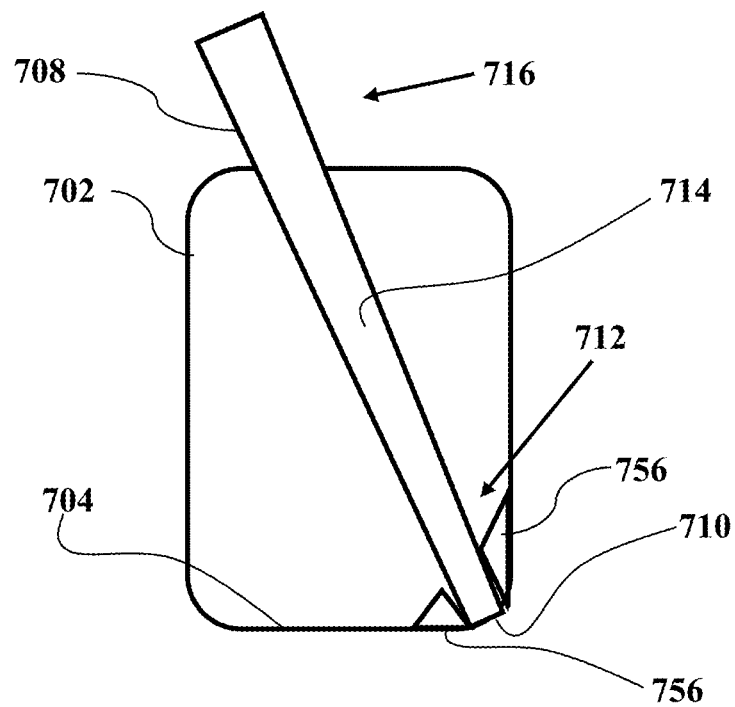
FIG. 7C provides a schematic cross-sectional illustration of the pipette tip and mixing vessel as shown in FIG. 7B. In this figure, the pipette tip is engaged with the raised feature having angled surfaces and a curved bottom, and the orifice of the pipette tip is occluded.

FIG. 7C provides a schematic cross-sectional illustration of the pipette tip 708 and mixing vessel 702 as shown in FIG. 7B. In this figure, the pipette tip 708 is engaged with the raised feature 756 having angled surfaces 703 and a curved bottom 705, and the orifice 710 of the pipette tip 708 is occluded. Application of pressure within internal cavity 714 of pipette tip 708 while orifice 710 remains occluded is effective to provide pressure build-up (whether positive or negative) within internal cavity 714, and to provide increased fluid flow through orifice 710 upon release of the occlusion of orifice 710.

Figure 7D:
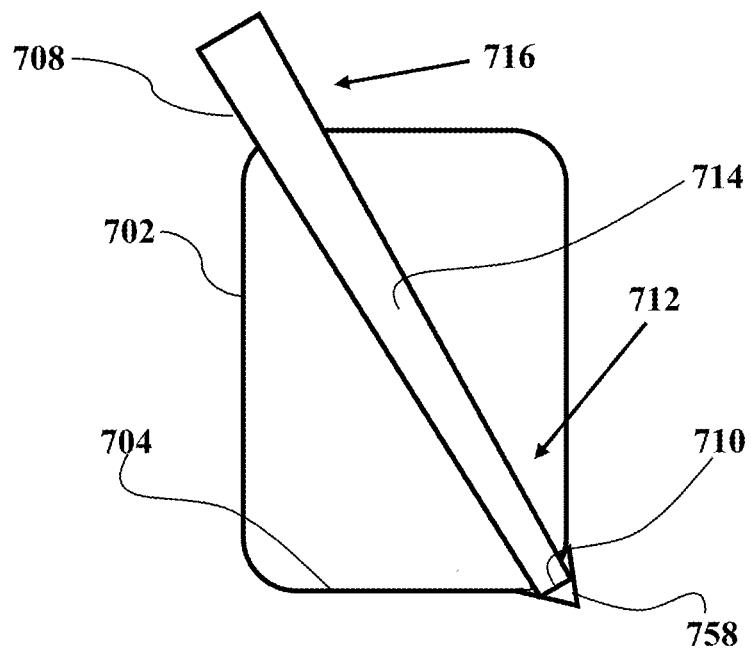
FIG. 7D provides a schematic cross-sectional illustration of the pipette tip and mixing vessel similar to the ones shown in FIGS. 7A-7C, except that, instead of having raised features, the mixing vessel has a depression into which the pipette tip may be pressed. In this figure, the pipette tip is engaged with the depression, and the orifice of the pipette tip is occluded.

FIG. 7D provides a schematic cross-sectional illustration of the pipette tip and mixing vessel similar to the ones shown in FIGS. 7A-7C, except that, instead of having raised features, the mixing vessel 702 has a depression 758 (shown here in the lower right corner of the mixing vessel 702). In this figure, the pipette tip 708 is engaged with the depression 758, and the orifice 710 of the pipette tip 708 is occluded. Application of pressure within internal cavity 714 of pipette tip 708 while orifice 710 remains occluded is effective to provide pressure build-up (whether positive or negative) within internal cavity 714, and to provide increased fluid flow through orifice 710 upon release of the occlusion of orifice 710.

Figure 7E:
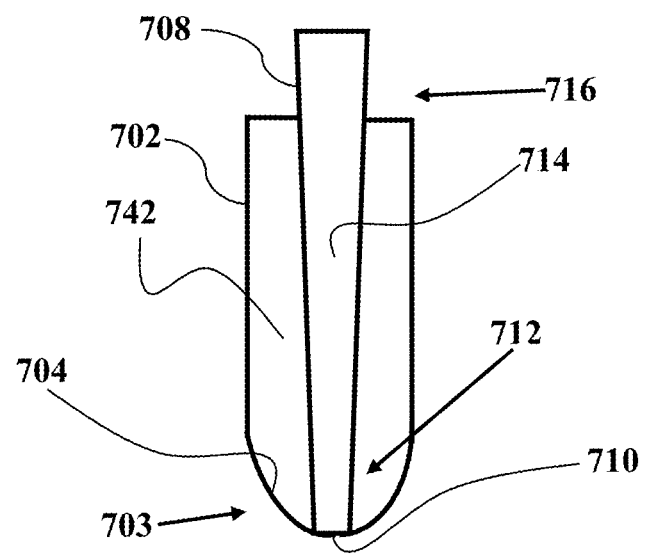
FIG. 7E provides a schematic cross-sectional illustration of a pipette tip within a mixing vessel, the mixing vessel having a curved inner surface at its distal end. In this figure, the pipette tip is engaged with the inner surface of the mixing vessel, and the orifice of the pipette tip is occluded by the engagement.

FIG. 7E provides a schematic cross-sectional illustration of a pipette tip 708 disposed partly within a mixing vessel 702, pipette tip 708 having a proximal portion 716, a distal portion 712, and an internal cavity 714 connected with an orifice 710 on the distal portion 712. The mixing vessel 702 has a curved inner surface 704 at its distal end 707. In this figure, the pipette tip 708 is engaged with the inner surface 704 of the mixing vessel 702, and the orifice 710 of the pipette tip 708 is occluded by the engagement. Application of pressure within internal cavity 714 of pipette tip 708 while orifice 710 remains occluded is effective to provide pressure build-up (whether positive or negative) within internal cavity 714, and to provide increased fluid flow through orifice 710 upon release of the occlusion of orifice 710.

In any of the embodiments shown in the figures, and in any embodiment of the pipette tips suitable for use as disclosed herein, an orifice may be substantially circular, and may have a diameter of one or a few millimeters; for example, an orifice of a pipette tip suitable for use as disclosed herein may have a substantially circular opening having a diameter of about 0.1 mm, or about 0.2 mm, or about 0.3 mm, or about 0.4 mm, or about 0.5 mm, or about 0.6 mm, or about 0.7 mm, or about 0.8 mm, or about 0.9 mm, or about 1 mm, or about 1.2 mm, or about 1.5 mm, or about 2 mm, or about 3 mm, or about 4 mm, or about 5 mm, or about 8 mm, or about 10 mm, or about 20 mm, or about 30 mm, or more. In embodiments, an orifice of a pipette tip suitable for use as disclosed herein may have an oblong-shaped opening, e.g., oval or elliptical in shape, having a long axis of about 0.1 mm, or about 0.2 mm, or about 0.3 mm, or about 0.4 mm, or about 0.5 mm, or about 0.6 mm, or about 0.7 mm, or about 0.8 mm, or about 0.9 mm, or about 1 mm, or about 1.2 mm, or about 1.5 mm, or about 2 mm, or about 3 mm, or about 4 mm, or about 5 mm, or about 8 mm, or about 10 mm, or about 20 mm, or about 30 mm, or more. In embodiments, an orifice of a pipette tip suitable for use as disclosed herein may have a rectangularly shaped opening (e.g., a slot or slit), or a star-shaped opening, or an opening of any other suitable shape. Such rectangularly shaped, or star-shaped, or other shaped openings of an orifice of a pipette tip suitable for use as disclosed herein may have a long axis of about 0.1 mm, or about 0.2 mm, or about 0.3 mm, or about 0.4 mm, or about 0.5 mm, or about 0.6 mm, or about 0.7 mm, or about 0.8 mm, or about 0.9 mm, or about 1 mm, or about 1.2 mm, or about 1.5 mm, or about 2 mm, or about 3 mm, or about 4 mm, or about 5 mm, or about 8 mm, or about 10 mm, or about 20 mm, or about 30 mm, or more.

In embodiments, a pipette tip may be pressed against an inner surface of a mixing vessel, occluding the orifice of the pipette tip, for a short period of time. In embodiments, such a short period of time may be a period of time of less than about 1 or a few seconds. In embodiments, the short period of may be less than about three-quarters of a second, or may be less than about half of a second. In embodiments, the short period of time is longer than about one to ten milliseconds; in embodiments, the short period of time is longer than about 10 to 20 milliseconds; in embodiments, the short period of time is longer than about 10 to 100 milliseconds. For example, a pipette tip may be pressed against an inner surface of a mixing vessel, occluding the orifice of the pipette tip, for a period of time of between about 10 milliseconds and about 10 seconds. In embodiments, a pipette tip may be pressed against an inner surface of a mixing vessel, occluding the orifice of the pipette tip, for a period of time of between about 10 milliseconds and about 3 seconds. In embodiments, a pipette tip may be pressed against an inner surface of a mixing vessel, occluding the orifice of the pipette tip, for a period of time of between about 10 milliseconds and about 2 seconds. In embodiments, a pipette tip may be pressed against an inner surface of a mixing vessel, occluding the orifice of the pipette tip, for a period of time of between about 10 milliseconds and about 1 second. In embodiments, a pipette tip may be pressed against an inner surface of a mixing vessel, occluding the orifice of the pipette tip, for a period of time of between about 20 milliseconds and about 2 seconds. In embodiments, a pipette tip may be pressed against an inner surface of a mixing vessel, occluding the orifice of the pipette tip, for a period of time of between about 20 milliseconds and about 1 second. In embodiments, a pipette tip may be pressed against an inner surface of a mixing vessel, occluding the orifice of the pipette tip, for a period of time of between about 30 milliseconds and about 3 seconds. In embodiments, a pipette tip may be pressed against an inner surface of a mixing vessel, occluding the orifice of the pipette tip, for a period of time of between about 30 milliseconds and about 2 seconds. In embodiments, a pipette tip may be pressed against an inner surface of a mixing vessel, occluding the orifice of the pipette tip, for a period of time of between about 30 milliseconds and about 1 second. In embodiments, a pipette tip may be pressed against an inner surface of a mixing vessel, occluding the orifice of the pipette tip, for a period of time of between about 50 milliseconds and about 2 seconds. In embodiments, a pipette tip may be pressed against an inner surface of a mixing vessel, occluding the orifice of the pipette tip, for a period of time of between about 50 milliseconds and about 1 second. In embodiments, a pipette tip may be pressed against an inner surface of a mixing vessel, occluding the orifice of the pipette tip, for a period of time of between about 100 milliseconds and about 5 seconds. In embodiments, a pipette tip may be pressed against an inner surface of a mixing vessel, occluding the orifice of the pipette tip, for a period of time of between about 100 milliseconds and about 3 seconds. In embodiments, a pipette tip may be pressed against an inner surface of a mixing vessel, occluding the orifice of the pipette tip, for a period of time of between about 100 milliseconds and about 2 seconds. In embodiments, a pipette tip may be pressed against an inner surface of a mixing vessel, occluding the orifice of the pipette tip, for a period of time of between about 100 milliseconds and about 1 second.

In embodiments, a pipette tip that is pressed against an inner surface of a mixing vessel while pressure is applied to the interior of the pipette tip, occluding the orifice of the pipette tip, may generate an additional pressure build-up within the pipette tip of up to about 100% to 200% of the pressure that would be built-up within the pipette tip in the absence of occlusion; that is, the pressure within the pipette tip may be 200% to about 300% of the pressure that would be built-up within the pipette tip in the absence of occlusion. For example, applying pressure to the interior of a pipette tip whose orifice is occluded by being pressed against an interior surface of a mixing vessel may generate an additional pressure build-up within the pipette tip of between about 10% to about 150% of the pressure that would be built-up within the pipette tip in the absence of occlusion, that is, the pressure within the pipette tip may be 110% to about 250% of the pressure that would be built-up within the pipette tip in the absence of occlusion. In embodiments, applying pressure to the interior of a pipette tip whose orifice is occluded by being pressed against an interior surface of a mixing vessel may generate a pressure build-up within the pipette tip of between about 120% to about 200% of the pressure that would be built-up within the pipette tip in the absence of occlusion. In embodiments, applying pressure to the interior of a pipette tip whose orifice is occluded by being pressed against an interior surface of a mixing vessel may generate a pressure build-up within the pipette tip of between about 125% to about 175% of the pressure that would be built-up within the pipette tip in the absence of occlusion. In embodiments, applying pressure to the interior of a pipette tip whose orifice is occluded by being pressed against an interior surface of a mixing vessel may generate a pressure build-up within the pipette tip of between about 130% to about 170% of the pressure that would be built-up within the pipette tip in the absence of occlusion. In embodiments, applying pressure to the interior of a pipette tip whose orifice is occluded by being pressed against an interior surface of a mixing vessel may generate a pressure build-up within the pipette tip of between about 150% to about 175% of the pressure that would be built-up within the pipette tip in the absence of occlusion.

As discussed above, removal of the pipette tip from contact with the internal surface of a mixing vessel (i.e., removing the occlusion of the orifice) allows fluid flow through the orifice of the pipette tip, and allows mixing of fluids in the mixing vessel, the pipette tip, or both. The additional pressure built-up within the pipette tip provides additional mixing, and improved mixing, as compared to the mixing that would occur in the absence of occlusion of the pipette tip orifice. In embodiments, compressed gas within the pipette tip, or within the nozzle, or within tubing or a reservoir in fluid continuity with the pipette tip interior may expand upon removal of the occlusion of the orifice, and drive fluid flow through the orifice (whether directly or indirectly); in embodiments, such fluid flow driven by a compressed gas may aid in providing greater mixing as compared to the mixing that would occur in the absence of occlusion of the pipette tip orifice.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, and other ranges.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2014-2015 Thermos, Inc.

What is claimed is:

1. A method of mixing a fluid, comprising:

Pressing a pipette tip of against an inner surface of a mixing vessel, wherein i) said pipette tip has an interior passage therethrough, a distal end with a lip defining an orifice, wherein said orifice is continuous with and connected to said interior passage, and a proximal end connected to said interior passage and configured to engage with a nozzle; and ii) the pipette tip is held by a nozzle, said nozzle comprising an operable fluid connection with a source of positive-pressure or suction; and wherein when a pipette tip is held by said nozzle, an operable fluid connection is provided between the nozzle, the orifice, the interior passage, the distal portion and said source of positive-pressure or suction;

wherein said pressing presses said lip against said inner surface of said mixing vessel, effective to occlude the orifice;

Applying pressure to fluid within one or more of the nozzle, the distal portion, the interior passage, and the orifice;

Removing said pipette tip from contact with said inner surface of the mixing vessel, effective to remove said occlusion of said orifice effective that fluid flows through said orifice;

Whereby fluid is mixed within the mixing vessel.

2. The method of claim 1, wherein said pressure is positive pressure effective to induce fluid flow out of said orifice and into said mixing vessel.

3. The method of claim 1, wherein said pressure is negative pressure effective to induce fluid flow into said orifice and out of said mixing vessel.

4. The method of claim 1, wherein said mixing vessel contains a first fluid, and said fluid handling apparatus contains a second fluid, and said fluid flow is effective to mix said first fluid and said second fluid.

5. The method of claim 4, wherein said mixing comprises i) applying positive pressure after applying negative pressure, effective to induce fluid flow out of said orifice and into said mixing vessel, effective to mix said first fluid and said second fluid within said mixing vessel, ii) applying negative pressure after applying positive pressure, effective to induce fluid flow into said orifice and out of said mixing vessel following expulsion of fluid from the pipette tip, or iii) both i) and ii).

6. The method of claim 4, wherein said applying pressure comprises alternating application of negative pressure and positive pressure, effective to aspirate fluid from said pipette tip orifice during application of negative pressure, and effective to expel fluid into said pipette tip orifice during application of positive pressure, wherein said mixing said first fluid and said second fluid comprises mixing within said mixing vessel.

7. The method of claim 1, wherein said nozzle comprises a nozzle of an automatic sample analysis device.

8. The method of claim 1,
wherein said pipette is operably connected to an automated pipette mechanism, said automated pipette mechanism comprising part of an automatic sample analysis device.

9. The method of claim 8, comprising alternating application of positive pressure and of negative pressure, wherein said alternating comprises a) applying positive pressure following application of negative pressure, wherein applying positive pressure is effective to expel fluid from said pipette tip through said orifice and into said mixing vessel, or b) applying negative pressure following said application of positive pressure, wherein applying negative pressure is effective to aspirate fluid from said mixing vessel and into said pipette tip through said orifice.

10. The method of claim 8, wherein i) the inner surface of the mixing vessel has a protrusion which extends into the interior of the mixing vessel, wherein said protrusion is configured to engage and occlude an orifice of a pipette tip when a pipette tip is placed onto or over the protrusion, ii) the inner surface of the mixing vessel has a depression which extends away from the rest of the interior of the mixing vessel, wherein said depression is configured to engage and occlude an orifice of a pipette tip when a pipette tip is placed onto or into the depression, or iii) both i) and ii).

* * * * *